(12) United States Patent
Kirkland et al.

(10) Patent No.: US 9,968,076 B2
(45) Date of Patent: May 15, 2018

(54) TRANSGENIC ANIMALS CAPABLE OF BEING INDUCED TO DELETE SENESCENT CELLS

(71) Applicant: Mayo Foundation for Medical Education and Research, Rochester, MN (US)

(72) Inventors: James L. Kirkland, Rochester, MN (US); Tamar Tchkonia, Rochester, MN (US); Jan M. A. van Deursen, Rochester, MN (US); Darren J. Baker, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days. days.

(21) Appl. No.: 14/792,208

(22) Filed: Jul. 6, 2015

(65) Prior Publication Data
US 2015/0296755 A1 Oct. 22, 2015

Related U.S. Application Data

(63) Continuation of application No. 14/125,841, filed as application No. PCT/US2012/043613 on Jun. 21, 2012, now abandoned.

(60) Provisional application No. 61/567,587, filed on Dec. 6, 2011, provisional application No. 61/499,616, filed on Jun. 21, 2011.

(51) Int. Cl.
| | | |
|---|---|---|
| A01K 67/027 | (2006.01) | |
| C07K 14/435 | (2006.01) | |
| C12N 15/62 | (2006.01) | |
| A61K 49/00 | (2006.01) | |

(52) U.S. Cl.
CPC ...... *A01K 67/0275* (2013.01); *A61K 49/0008* (2013.01); *C07K 14/435* (2013.01); *C12N 15/62* (2013.01); *A01K 2217/052* (2013.01); *A01K 2217/203* (2013.01); *A01K 2227/105* (2013.01); *A01K 2267/03* (2013.01); *C07K 2319/00* (2013.01)

(58) Field of Classification Search
CPC .......... A01K 67/0275; A01K 2227/105; A01K 2267/03; A01K 2267/0373; C12N 15/8509; C12N 2015/8527; C12N 2830/008
USPC .................................................. 800/18, 3, 9
See application file for complete search history.

(56) References Cited

U.S. PATENT DOCUMENTS

| | | | |
|---|---|---|---|
| 4,873,191 A | 10/1989 | Wagner et al. | |
| 6,201,020 B1 | 3/2001 | Zhang et al. | |
| 7,390,799 B2 | 6/2008 | Bruncko et al. | |
| 7,642,260 B2 | 1/2010 | Bruncko et al. | |
| 7,767,684 B2 | 8/2010 | Bruncko et al. | |
| 7,829,556 B2 | 11/2010 | Bemis et al. | |
| 7,842,681 B2 | 11/2010 | Elmore et al. | |
| 7,851,626 B2 | 12/2010 | Ding et al. | |
| 7,879,857 B2 | 2/2011 | Mabire et al. | |
| 7,928,104 B2 | 4/2011 | Mabire et al. | |
| 7,973,161 B2 | 7/2011 | Bruncko et al. | |
| 8,071,623 B2 | 12/2011 | Jones et al. | |
| 8,168,645 B2 | 5/2012 | Baell et al. | |
| 8,343,967 B2 | 1/2013 | Ding et al. | |
| 8,426,422 B2 | 4/2013 | Hexamer et al. | |
| 8,518,970 B2 | 8/2013 | Baell et al. | |
| 8,541,417 B2 | 9/2013 | Brown et al. | |
| 8,557,983 B2 | 10/2013 | Bruncko et al. | |
| 8,563,735 B2 | 10/2013 | Bruncko et al. | |
| 8,586,754 B2 | 11/2013 | Bruncko et al. | |
| 8,614,318 B2 | 12/2013 | Bruncko et al. | |
| 8,624,027 B2 | 1/2014 | Shah et al. | |
| 2004/0006233 A1 | 1/2004 | Holt et al. | |
| 2004/0180430 A1 | 9/2004 | West et al. | |
| 2005/0019865 A1 | 1/2005 | Kihm et al. | |
| 2005/0181076 A1 | 8/2005 | Ziegler | |
| 2007/0099186 A1 | 5/2007 | D' Adda Di Fagagna et al. | |
| 2008/0108062 A1 | 5/2008 | Sharpless et al. | |
| 2008/0216180 A1 | 9/2008 | Abate-Shen et al. | |
| 2008/0221132 A1 | 9/2008 | Cai et al. | |
| 2008/0234362 A1 | 9/2008 | Chandler | |
| 2009/0019554 A1 | 1/2009 | Selkirk et al. | |
| 2009/0022465 A1 | 1/2009 | Chen et al. | |
| 2009/0193533 A1* | 7/2009 | Edge et al. | 800/18 |
| 2009/0281129 A1 | 11/2009 | Chang et al. | |
| 2010/0016218 A1 | 1/2010 | Lichter et al. | |

(Continued)

FOREIGN PATENT DOCUMENTS

| | | |
|---|---|---|
| WO | WO 2003/028443 | 4/2003 |
| WO | WO 2006/018632 | 2/2006 |

(Continued)

OTHER PUBLICATIONS

Baker et al. (2008) Nat. Cell. Biol., vol. 10(7), 825-836, including Supplementary Information.*
Pajvani et al. (2005) Nat. Med., vol. 11(7), 797-803.*
Wang et al. (2001) J. Biol. Chem., vol. 276, 48655-48661.*
Baker et al., "BubR1 insufficiency causes early onset of aging-associated phenotypes and infertility in mice," *Nat. Genet.*, 2004, 36:744-749.
Baker et al., "Clearance of p16Ink4a-positive senescent cells delays ageing-associated disorders," *Nature*, Nov. 10, 2011, 479:232-237.
Campisi, "Cellular senescence: putting the paradoxes in perspective," *Curr. Opin. Genet. Dev.*, 2011, 1:107-112.
Campisi, "Senescent cells, tumor suppression, and organismal aging: good citizens, bad neighbors," *Cell*, Feb. 2005, 120:513-522.
Cibelli et al., "Cloned transgenic calves produced from nonquiescent fetal fibroblasts," *Science*, 1998, 208:1256-1258.
Coppe et al., "Senescence-associated secretory phenotypes reveal cell-nonautonomous functions of oncogenic RAS and the p53 tumor suppressor," *PLoS Biol.*, 2008, 6:2853-2868.

(Continued)

*Primary Examiner* — Anne Marie S Wehbe
(74) *Attorney, Agent, or Firm* — Fish & Richardson P.C.

(57) ABSTRACT

This document provides a transgenic mouse for studying the role of senescent cells in an age-related phenotype. A recombinant polypeptide is expressed in senescent cells under control of a p16INK4a promoter. The polypeptide can be triggered to directly induce cell death in senescent cells. As a result, progression of one or more age-related phenotypes is delayed in the mouse. An example is the INK-ATTAC mouse which also expresses a marker polypeptide in senescent cells.

31 Claims, 18 Drawing Sheets

(56) References Cited

U.S. PATENT DOCUMENTS

| | | |
|---|---|---|
| 2010/0125064 A1 | 5/2010 | Boettcher et al. |
| 2010/0190807 A1 | 7/2010 | Porter et al. |
| 2010/0260733 A1 | 10/2010 | Qi |
| 2010/0292200 A1 | 11/2010 | Kile et al. |
| 2010/0310504 A1 | 12/2010 | Lowe et al. |
| 2011/0023137 A1 | 1/2011 | Chu et al. |
| 2011/0189142 A1 | 8/2011 | May et al. |
| 2011/0212909 A1 | 9/2011 | Wen et al. |
| 2012/0108590 A1 | 5/2012 | Birtalan et al. |
| 2012/0156134 A1 | 6/2012 | Squires |
| 2013/0096121 A1 | 4/2013 | Wang et al. |
| 2013/0267534 A1 | 10/2013 | Bruncko et al. |
| 2013/0287763 A1 | 10/2013 | Sathyabarayanan et al. |
| 2013/0288980 A1 | 10/2013 | De et al. |
| 2013/0302283 A1 | 11/2013 | Kihm |
| 2014/0017341 A1 | 1/2014 | Gourlaouen |
| 2014/0073640 A1 | 3/2014 | Judd et al. |
| 2014/0189897 A1 | 7/2014 | Kirkland |
| 2014/0275082 A1 | 9/2014 | Tao et al. |
| 2014/0329854 A1 | 11/2014 | Larsen |
| 2014/0378683 A1 | 12/2014 | Porter |
| 2015/0044184 A1 | 2/2015 | Chen et al. |
| 2015/0056195 A1 | 2/2015 | Bertolotto |
| 2015/0064137 A1 | 3/2015 | Lichtsteiner et al. |
| 2015/0072950 A1 | 3/2015 | Sauve et al. |
| 2015/0072972 A1 | 3/2015 | Mevellec et al. |
| 2015/0140036 A1 | 5/2015 | Mannick et al. |
| 2015/0151001 A1 | 6/2015 | Squires |
| 2015/0210717 A1 | 7/2015 | Gunes et al. |
| 2017/0027139 A1 | 2/2017 | Van Deursen et al. |
| 2017/0042129 A1 | 2/2017 | Campisi et al. |

FOREIGN PATENT DOCUMENTS

| | | |
|---|---|---|
| WO | WO 2008/113131 | 9/2008 |
| WO | WO 2009/039553 | 4/2009 |
| WO | WO 2009/085216 | 7/2009 |
| WO | WO 2009/105234 | 8/2009 |
| WO | WO 2010/000491 | 1/2010 |
| WO | WO 2010/134790 | 11/2010 |
| WO | WO 2010/148447 | 12/2010 |
| WO | WO 2011/068561 | 6/2011 |
| WO | WO 2011/150016 | 12/2011 |
| WO | WO 2013/152038 | 10/2013 |
| WO | WO 2013/170174 | 11/2013 |
| WO | WO 2014/041125 | 3/2014 |
| WO | WO 2014/186878 | 11/2014 |
| WO | WO 2015/044649 | 4/2015 |
| WO | WO 2015/051766 | 4/2015 |
| WO | WO 2015/066442 | 5/2015 |
| WO | WO 2015/070280 | 5/2015 |
| WO | WO 2015/073644 | 5/2015 |

OTHER PUBLICATIONS

Dimri et al., "A biomarker that identifies senescent human cells in culture and in aging skin in vivo," Proc. Natl. Acad. Sci. USA, Sep. 1995, 92:9363-9367.

Drabek et al., "The expression of bacterial nitroreductase in transgenic mice results in specific cell killing by the prodrug CB1954," Gene Therapy, Feb. 1997, 4(2):93-100.

Gan et al., "PPAR{gamma} accelerates cellular senescence by inducing p16INK4 {alpha} expression in human diploid fibroblasts," J. Cell Sci., 2008, 121:2235-2245.

Guatelli et al., "Isothermal, in vitro amplification of nucleic acids by a multienzyme reaction modeled after retroviral replication," Proc. Natl. Acad. Sci. USA, Mar. 1990, 87:1874-1878.

Handschin et al., "Skeletal muscle fiber-type switching, exercise intolerance, and myopathy in PGC-1alpha muscle-specific knockout animals," J. Biol. Chem., 2007, 282:30014-30021.

Hartman et al., "Mutant mice with small amounts of BubR1 display accelerated age-related gliosis," Neurobiol. Aging, 2007, 28:921-927.

Kirkland et al., "Effects of fat depot site on differentiation-dependent gene expression in rat preadipocytes," Int. J. Obes. Relat. Metab. Disord., 1996, 20(Suppl 3):S102-107.

Krishnamurthy et al., "Ink4a/Arf expression is a biomarker of aging," J. Clin. Invest., 2004, 114:1299-1307.

Krtolica et al., "Senescent fibroblasts promote epithelial cell growth and tumorigenesis: A link between cancer and aging," Proc Natl Acad Sci U S A, 2001, 98(21):12072-12077.

Kuilman et al., "The essence of senescence," Genes Develop., 2010, 24:2463-2479.

Le et al., "Ionizing radiation-induced long-term expression of senescence markers in mice is independent of p53 and immune status," Aging Cell, 2010, 9(3):398-409.

LeBrasseur et al., "Myostatin inhibition enhances the effects of exercise on performance and metabolic outcomes in aged mice," J. Gerontol. A. Biol. Sci. Med. Sci., 2009, 64:940-948.

Lewis, "PCR's Competitors are alive and well and moving rapidly towards commercialization," Genetic Engineering News, 1992, 12:1, 2 pages.

Lo, "Transformation by iontophoretic microinjection of DNA: multiple integrations without tandem insertions," Mol. Cell. Biol., 1983, 3:1803-1814.

Matsumoto et al., "Aging-associated vascular phenotype in mutant mice with low levels of BubR1," Stroke, 2007, 38:1050-1056.

Soleimani and Nadri, "A protocol for isolation and culture of mesenchymal stem cells from mouse bone marrow," Nat. Protoc., 2009, 4:102-106.

Thompson et al., "Germ line transmission and expression of a corrected HPRT gene produced by gene targeting in embryonic stem cells," Cell, 1989, 56:313-321.

Van der Putten et al., "Efficient insertion of genes into the mouse germ line via retroviral vectors," Proc. Natl. Acad. Sci. USA, 1985, 82:6148-1652.

Wakayama et al., "Full-term development of mice from enucleated oocytes injected with cumulus cell nuclei," Nature, 1988, 394:369-374.

Wang et al., "PANIC-ATTAC: a mouse model for inducible and reversible beta-cell ablation," Diabetes, Aug. 2008, 57(8):2137-48.

Weiss, "Hot prospect for new gene amplifier," Science, 1991, 254:1292-1293.

Wilmut et al., "Viable offspring derived from fetal and adult mammalian cells," Nature, 1997, 385:810-813.

International Preliminary Report in International Application No. PCT/US2012/043613, dated Jan. 9, 2014, 5 pages.

International Search Report and Written Opinion in International Application No. PCT/US2012/043613, dated Nov. 29, 2012, 9 pages.

Ambroggio and Kuhlman, "Design of protein conformational switches," Curr Opin Struct Biol.,16:525-530, 2006.

Baker et al., "Naturally occurring p16Ink4a-positive cells shorten healthy lifespan," Nature., 530(7589):184-189, 30 pages, Feb. 11, 2016.

Binkowski et al., "Ligand-Regulated Peptides: A General Approach for Modulating Protein-Peptide Interactions with Small Molecules," Chem Biol., 12:847-855, Jul. 2005.

Buskirk and Liu, "Creating Small-Molecule-Dependent Switches to Modulate Biological Functions," Chem Biol., 12:151-161, Feb. 2005.

Demaria et al., "An Essential Role for Senescent Cells in Optimal Wound Healing through Secretion of PDGF-AA," Dev Cell., 31(6):722-733, Dec. 22, 2014.

Fegan et al., "Chemically Controlled Protein Assembly: Techniques and Applications," Chem Rev., 110:3315-3336, 2010.

Gross et al., "Enforced dimerization of BAX results in its translocation, mitochondrial dysfunction and apoptosis," EMBO J., 17(14):3878-3885, Jul. 15, 1998.

Liu et al., "Dimerization of two novel apoptosisinducing proteins and its function in regulating cell apoptosis," Sci Chine C Life Sci., 46(3):225-234, Jun. 2003.

Abate-Daga, et al., "Oncolytic adenoviruses armed with thymidine kinase can be traced by PET imaging and show potent antitumoural effects by ganciclovir dosing," PLoS One., 6(10):e26142, Oct. 18, 2011.

(56) References Cited

OTHER PUBLICATIONS

Adams., "Healing and hurting: molecular mechanisms, functions, and pathologies of cellular senescence," Mol Cell., 36(1):2-14, Oct. 9, 2009.
Bazarov et al., "P16INK4a Mediated Suppression of telomerase in normal and malignant human breast cells," Aging Cell., 9(5):736-746, Oct. 2010.
BEAUSEJOURet al., "Reversal of human cellular senescence: roles of the p53 and p16 pathways," EMBO J., 22(16):4212-4222, Aug. 15, 2003.
Bennett, et al., "SP600125, an Anthrapyrazolone Inhibitor of Jun N-Terminal Kinase," PNAS., 98(24):13681-13686, Nov. 20, 2001.
Campisi, et al., "Cellular senescence: a link between cancer and age-related degenerative disease?" Semin Cancer Biol., 21(6):354-359, Dec. 2011.
Campisi, et al., "Cellular senescence: when bad things happen to good cells," Nature Reviews Molecular Cell Biology., 8:729-740, 2007.
Chang, et al., "Effects of p21 Wafl/Cipl/Sdilon cellular gene expression: Implications for carcinogenesis, senescence, and age-related diseases," PNAS., 97(8):4291-4296, 2000.
Chung, et al., "Molecular inflammation: underpinnings of aging and age-related diseases," Ageing Res Rev., 8(1):18-30, Jan. 2009.
Cibelli, et al., "Cloned transgenic calves produced from nonquiescent fetal fibroblasts," Science, 280:1256-1258, 1998.
Coppe et al., "Tumor Suppressor and Aging Biomarker p16INK4a Induces Cellular Senescence without the Associated Inflammatory Secretory Phenotype," J Biol Chem. 286(42):36396-36403, Oct. 21, 2011.
Davalos, et al., "p53-dependent release of Alarnain BMGB1 is a central mediator of senescent Phenotypes," J Cell Biol., 201(4):613-29, May 13, 2013.
Davalos, et al., "Senescent cells as a source of inflammatory factors for tumor progression," Cancer Metastasis Rev., 29(2):273-83, Jun. 2010.
Efeyan, et al., "Induction of p53-dependent senescence by the MDM2 antagonist nutlin-3a in mouse cells offibroblast origin," Cancer Res., 67(15):7350-7357, Aug. 1, 2007.
Freund, et al., "Inflammatoty networks during cellular senescence: causes and consequences," Trends Mol Med., 16(5):238-46, May 2010.
Freund, et at, "Lamin B1 loss is a senescence-associated biomarker," Mol Biol Cell., 23(11):2066-75, Jun. 2012.
Johnson, et al., "Somatic activation of the K-ras oncogene causes early onset lung cancer in mice," Nature., 410(6832):1111-1116, Apr. 26, 2001.
Kaina, B., "DNA damage-triggered apoptosis: critical role of DNA repair, double-strand breaks, cell proliferation and signaling," Biochem Pharmacol., 66(8):1547-54, Oct. 15, 2003.
Kim, et al., "SP600125, an inhibitor of Jnk pathway, reduces viability of relatively resistant cancer cells to doxorubicin," Biochem Biophys Res Commun., 387(3):450-455, Sep. 25, 2009.
Laberge, et al., "Glucocorticoids suppress selected components of the senescence-associated secretory phenotype," Aging Cell. 11(4):569-578, 2012.
Laberge, et al., "Mitochondrial DNA damage induces apoptosis in senescent cells," Cell Death Dis., 18;4:e727, Jul. 2013.
Lessene; et al., "Structure-guided design of a selective BCL-X(L) inhibitor," 9(6), 390-397, Jun. 2013.
Mallet, et al., "Conditional cell ablation by tight control of caspase-3 dimerization in transgenic mice," Nat Biotechnol. 20(12):1234-9, Dec. 2002.
Moody, et al., "Conditional activation of Neu in the mammary epithelium of transgenic mice results in reversible pulmonary metastasis," Cancer Cell., 2(6):451-61, Dec. 2002.
Naylor et al., "Senescent Cells: A Novel Therapeutic Target for Aging and Age-Related Diseases," Clin Pharmacol Ther., 93(1):105-116, Jan. 2013.
Notice of Allowance in U.S. Appl. No. 15/067,543, dated Oct. 13, 2017, 11 pages.
Office Action in U.S. Appl. No. 14/394,854, dated Jan. 26, 2018, 16 pages.
Prieur, et al., "Cellular senescence in vivo: a barrier to tumorigenesis," Cuff Opin Cell Biol., 20(2):150-5, Apr. 2008.
Ray, et al., "Imaging tri-fusion multimodality reporter gene expression in living subjects," Cancer Res., 64(4):1323-30, Feb. 15, 2004.
Rodier, et al., "Persistent DNA damage signaling triggers senescence-associated inflammatory cytokine secretion," Nat Cell Biol., 11 (8):973-9, Aug. 2009.
Roninson., "Tumor Cell Senescence in Cancer Treatment," Cancer Research., 63(11):2705-2715, 2003.
Schmitt, et al., "A senescence program controlled by p53 and p16INK4a contributes to the outcome of cancer therapy," Cell., 109(3):335-46, May 3, 2002.
Shangary, et al., "Temporal activation of p53 by a specific MDM2 inhibitor is selectively toxic to tumors and leads to complete tumor growth inhibition," Proc Natl Acad Sci USA., 105(10):3933-3938, Mar. 11, 2008.
Sharpless, et al., "Telomeres, stem cells, senescence, and cancer," Journal of Clinical Investigation., 113(2):160-168, 2004.
Sis, et al., "Accelerated expression of senescence associated cell cycle inhibitor p16INK4A in kidneys with glomerular disease," Kidney Int., 71 (3):218-26, Feb. 2007.
Stanley et al., "Senescence and the Healing Rates of Venous Ulcers," J Vasc Surg., 33(6):1206-11, Jun. 2001.
Tchkonia, et al., "Fat tissue, aging, and cellular senescence," Aging Cell., 9(5):667-84, Oct. 2010.
Te Poele, et al., "DNA damage is able to induce senescence in tumor cells in vitro and in vivo," Cancer Res., 62(6):1876-83, Mar. 15, 2002.
Tsuji, et al., "Alveolar cell senescence exacerbates pulmonary inflammation in patients with chronic obstructive pulmonary disease," Respiration., 80(1):59-70, 2010.
Zhao et al., "Small molecule inhibitors of MDM2-p53 and MDMX-p53 interactions as new cancer therapeutics," BioDiscovery, 8(4), 2013, 15 pages.
U.S. Appl. No. 13/975,217, dated Aug. 23, 2013, Campisi et al.
U.S. Appl. No. 13/975,179, dated Aug. 23, 2013, Campisi et al.
Agarwalla, et al., "Oncolytic herpes simplex virus engineering and preparation," Methods Mol Biol., 797:1-19, 2012.
Chistiakov., "How to fight with senescent cells?" Geriatr Gerontol Int., 11(2):233-235, Apr. 2011.
Deursen, "Senescent Cells as Drivers of Cancer & Aging," Mayo Clinic. NYU Dec. 2014. 55 pages.
Deursen, "The role of p16+ (senescent) cells in aging," Erice. Jun. 2015. 17 pages.
Deursen, "Understanding Senescence and Chromosomal Instability in Cancer and Aging," Mayo Clinic. Ohio State. Jan. 2015. 49 pages.
Deursen, et al., "Senescent cells have some nerve! Mayo Clinic," NCI. Mar. 2015. Rochester, MN. 15 pages.
Deursen, et al., "Senescent cells shorten health and life span," Mayo Clinic. Berlin. Feb. 2015. 30 pages.
Deursen, et al., "Senescent in aging and age-related disease: from mechanism to therapy," Mayo Clinic. ICSA Conference. Jul. 2015. Santiago de Compostela. 40 pages.
Deursen. "Clearance of senescent cells and adult aging phenotypes," Pitts., Jun. 2014. 15 pages.
International search report and written opinion for PCT/US2013/072938, dated Apr. 22, 2014, 17 pages.
International search report and written opinion for PCT/US2012/069601, dated Apr. 30, 2013, 12 pages.
International search report and written opinion for PCT/US2015/013376, dated May 6, 2015, 9 pages.
International search report and written opinion for PCT/US2015/013387, dated Jun. 29, 2015, 34 pages.
International search report and written opinion for PCT/US2013/035023, dated Aug. 13, 2013, 10 pages.
International Search Report and Written Opinion for PCT/US2013/035020, dated Jul. 22, 2013, 9 pages.
Nasu, et al., "Suicide gene therapy for urogenital cancer: current outcome and prospects," Mol Urol., 4(2):67-71, 2000.

(56) References Cited

OTHER PUBLICATIONS

Office action for U.S. Appl. No. 12/809,952, dated Jan. 9, 2015, 4 pages.
Office action for U.S. Appl. No. 12/809,952, dated May 30, 2014, 8 pages.
Office action for U.S. Appl. No. 13/975,179, dated Sep. 11, 2015, 13 pages.
Office action for U.S. Appl. No. 13/975,217, dated Sep. 25, 2015, 19 pages.
Office action for U.S. Appl. No. 13/830,790, Nov. 25, 2014, pages.

\* cited by examiner

Figure 6
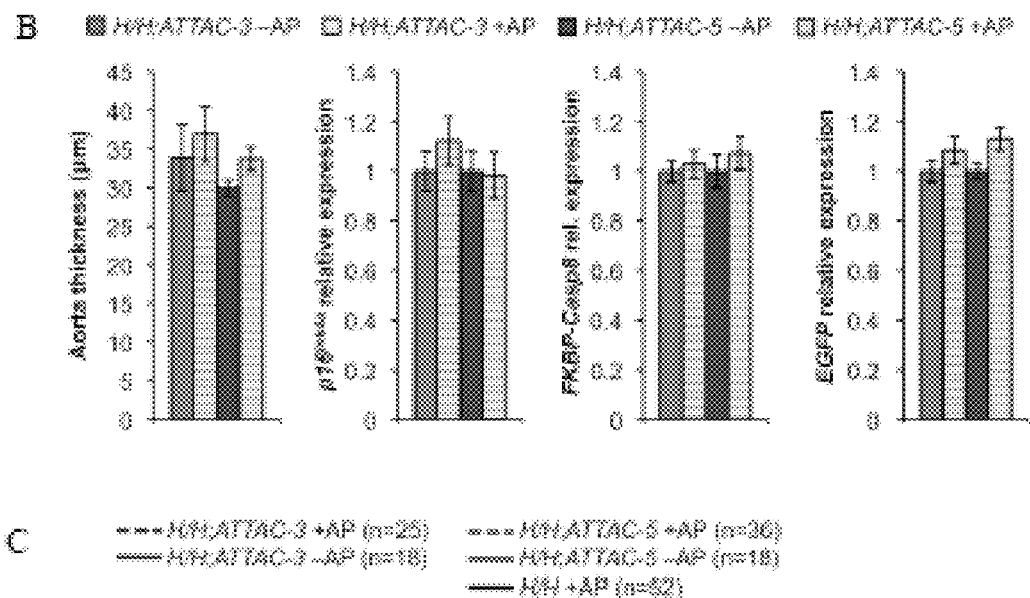
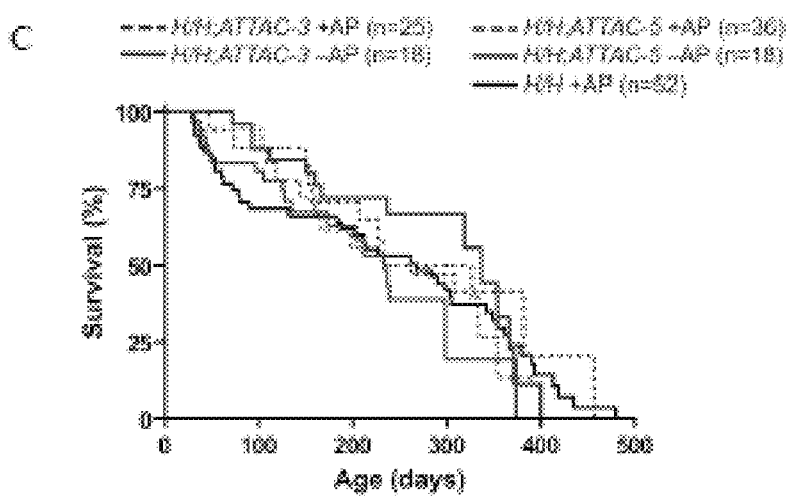

Figure 9

```
Entire 9267 nt sequence, uninterrupted ctaaattgtaagcgttaatattttgttaaaattcgcgttaaattttgttaaatcagctcattt
tttaaccaataggccgaaatcggcaaaatcccttataaatcaaaagaatagaccgagatagggt
tgagtgttgttccagtttggaacaagagtccactattaaagaacgtggactccaacgtcaaagg
gcgaaaaaccgtctatcagggcgatggcccactacgtgaaccatcaccctaatcaagtttttg
gggtcgaggtgccgtaaagcactaaatcggaaccctaaagggagccccgatttagagcttgac
ggggaaagccggcgaacgtggcgagaaaggaagggaagaaagcgaaggagcgggcgctagggc
gctggcaagtgtagcggtcacgctgcgcgtaaccaccacacccgccgcgcttaatgcgccgcta
cagggcgcgtcccattcgccattcaggctgcgcaactgttgggaagggcgatcggtgcgggcct
cttcgctattacgccagctggcgaaaggggqgatgtgctgcaaggcgattaagttgggtaacgcc
agggttttcccagtcacgacgttgtaaaacgacggccagtgagcgcgcgtaatacgactcacta
tagggcgaattggagctccaccgcggtggcggccgctctagaactagtgGATCCGTGTAAAGTC
ACTGCTTTTATAGCTACATCTGCATAGATCCCCTGTATGAAAGCATGTACTACCTGGATAATAA
TATCTGTATTTTTCTGTAGTAGGAAATCAGTGTAGTTTTTAAAACCAAAAAGTATTGTTATTAA
TCTATCTTTGATCTCAAACAATTTCAATGACCTAGTATAGTGATTTCTACGGAAAGCCCTGCAA
TTTACTCAAAGCAGTTTTTAAATATTGTTTTAAAAGTGTGTGTGTGTGTGTGTGTGTGTGTGTG
TGTGTGTGTGGTGTTAAAGTCATTTTCAAACCCCTCACAATGTCTTGAATGTGACATTTGAGTC
ATTTATGGTAACTTATAACTCCTTTGAAGAAGTTATTCAGAATTGAGGTTCCAGACACACAAAT
GCACAATACACCATTTTTCCTTCCAGTTAACAATCAGAGGGCAACACTTATTTTTAAAGGAAAA
TCGACTCCATAAGGGACTTTATAAAGGGGTAGACATAAACCAGTATCAGGGATAAACTCTCCGT
TCCCCTGTTTAACCTAATTTTCCCAGGGCCATCCTGGAATACGAATTTTCTCTTGAAATACAGT
CAAAGAAAAAGTGGTAGGCTACAGAGCAGAGGAAACACTGGACACAGCGACCCACCCCAGAGTC
ACTTCCCTTAATCTAATGACTAGGTTTTTTCTGAAAGTTATTTGTTAGAACACAGGAACTTTT
GCGACCACAGTGATGCTTTTAGAGGGTTGAATCCTCAAAAAGAAAATTAATCGCAACTAGTAGA
AGGGAGATTACTTATTGATTCTTATAACTTCTGCAGGAATACACAGTTATGAGTTAGGGCAAAG
AGAAAATTGACTTTTAATATTCTCTATCACTAACATGAGAGAACATGTATGTGTTCCAAAATAA
TTTTTATTTATTGAAAACCCGCTATATACCTGGATTTTCACAGAATATTCATTACTCTCCAAAA
TGGCCTTTTCTAGGTGAATTTTATTTTCCTTACAGACCTCAAGAAGTTTACATAATTTACTTAA
ACCTGAGGAGAGAGAACAAAGCCTCAGAAAATTTACATAGTTTATTTAAACTAAACTCAGCTTG
CTTGGTAGCAGCTTCTAATCCCAGCAGTTAAAGAGACAGAAGCAGGGCCAACCTGGGGTATAAT
ATAAGGTGAGACTCTCCTTTCTTTCTCTCTGTCTCTGTCTGTCTCTGTCTCTGTGTGTGTGT
GTGTGTGTGTGTGTGTGTGTCTCCTCTCTCTCTCTCTCTCTCTCTCTCTCTCTCTCTCTCTCTG
TCTCTCTCTCCCTCCCCCTCCCTCCCTCTCCCCCTCCTCTCTCCCTCCCTCTCCCTCCCCCCCC
CCCACACATTTGAATTCGTGGAGTTGGTAAATGAGGGGTCAGTTCTCTGTCTGTCTGTAGTTTT
GTGTCCACAGGATATGACTGACATTCTCACCACACACATACAAAGTCAAAAATAGCTGTGGCCA
TATAAAGAATATGGGGAGAGAAAATTATTCAAAATCTGCAGAAAATAATGCCAGGCCTTTAATC
CTGGCACCCAGGAGGCAGAAGGGAGACAGAGTTCTGAGTTTATGCTGAGTTCCAGGAGTGGAAG
AAAGGGCCATTGCCTTTCTGGTGAGGACTGTCTTTTTAAATCCTCCCTTCTGTCCAGTACTGGT
AACTCTGCCCAAAGCGTGTTCTTCTTCCTGCCTCACAAGATTGCAAAGACGTTTTTAACGAACA
ATTTAAACCGGTGCAACGTTTATGCGCAGCACACCAACTCATTTAAACAAACAACAGCCCCATA
AAATAGAAATACTTTATAAGCAGATTGCCCTCCGATGACTTCACCCCGTCACTTTTTTATAGTT
GTGTACAGAATCCTAGCACTGATACAGCAACATCAGAAATGTTTCTGCAAATCCTTCGCAAAGA
TTCGGATTTCATACTGGGCGTGGTACCCTCCAAAATGAGTTGTTTGAGCTAGGGTTGTTGGGAT
CTCAGCTTGGCGAAGTTGTAGCTCTTTCTTCTGAATAAAAGATGACACAATTTTCTGCTAAGAT
```

Figure 9 (Continued)

```
GTTAAATACCTTAAGTTTCAGTGTAGTGATGAAAATTACCCTCCTTCGTTTTTCTAATACCTGG
GTGTTGCACTGGGGAGGAAGGAGAGATTTCGAGAAGGACTAGTTCACTTTCTCAGAAGACACGT
GTGCACTTCTTTGCTGTGCGGGTCCAGAAGGAGCCCAGCGTGTCAAAGGGTGACCAGGCATGGG
GGAGGGGTGTTAGCGTGGGTAGCAGGCGGGGCTGTCCGATCCTTTAGCGCTGTTTCAACGCCC
AGCTCTCCTCCTGAACCCTGCATCTCTTCTGTAGTCCGGGCTCCATCCCTTTCCCCTCCCCCAT
CCGGAGGTGGGGGGAACAGCAGTGTTTTCAGGGGTGTTCAATTCATGCTATATTCAGGGCAAAT
AGCGCCACCTATGGCGGGCTGTGGAGCCAGGTCAGGAGCAGAGTGTGGCTCCCCCCCCCCCCA
CACCATCCTCAGAGGAAGGAAGGAGGGACCCACTGGTCACACGACTGGGCGATTGGGCGGGCAC
TGAATCTCCGCGAGGAAAGCGAACTCGAGGAGAGCCATCACGCGTAGCatggggagtagcaaga
gcaagcctaaggaccccagccagcgctctagaggcgtccaagtcgaaaccattagtcccggcga
tggcagaacatttcctaaaaggggacaaacatgtgtcgtccattatacaggcatgttggaggac
ggcaaaaaggtggacagtagtagagatcgcaataaacctttcaaattcatgttgggaaaacaag
aagtcattagggatgggaggagggcgtggctcaaatgtccgtcggccaacgcgctaagctcac
catcagccccgactacgcatacggcgctaccggacatcccggaattattcccctcacgctacc
ttggtgtttgacgtcgaactgttgaagctcgagactagaggagtgcaggtggagactatctccc
caggagacgggcgcaccttccccaagcgcggccagacctgcgtggtgcactacaccgggatgct
tgaagatggaagaaagttgattcctcccgggacagaaacaagccctttaagtttatgctaggc
aagcaggaggtgatccgaggctgggaagaagggggttgcccagatgagtgtgggtcagagagcca
aactgactatatctccagattatgcctatggtgccactgggcacccaggcatcatcccaccaca
tgccactctcgtcttcgatgtggagcttctaaaactggaaactagtagtgaatcacagactttg
gacaaagtttaccaaatgaaaagcaaacctcggggatactgtctgatcatcaacaatcacaatt
ttgcaaaagcacgggagaaagtgcccaaacttcacagcattagggacaggaatggaacacactt
ggatgcaggggctttgaccacgacctttgaagagcttcattttgagatcaagcccacgatgac
tgcacagtagagcaaatctatgagattttgaaaatctaccaactcatggaccacagtaacatgg
actgcttcatctgctgtatcctctcccatggagacaagggcatcatctatggcactgatggaca
ggaggcccccatctatgagctgacatctcagttcactggtttgaagtgcccttcccttgctgga
aaacccaaagtgttttttattcaggcttgtcaggggataactaccagaaaggtatacctgttg
agactgattcagaggagcaaccctatttagaaatggatttatcatcacctcaaacgagatatat
cccggatgaggctgactttctgctggggatggccactgtgaataactgtgtttcctaccgaaac
cctgcagagggaacctggtacatccagtcactttgccagagcctgagagagcgatgtcctcgag
gcgatgatattctcaccatcctgactgaagtgaactatgaagtaagcaacaaggatgacaagaa
aaacatggggaaacagatgcctcagcctactttcacactaagaaaaaaacttgtcttcccttct
gatgattacaaggatgacgacgataagtgaggatcaacctcgaggaattcACGCGTTAATTAA
CTCGAGGTTTTCGAGGTCGACGGTATCGATAAGCTTGATATCGAATTCCGCCCCTCTCCCTCCC
CCCCCCCTAACGTTACTGGCCGAAGCCGCTTGGAATAAGGCCGGTGTGCGTTTGTCTATATGTT
ATTTTCCACCATATTGCCGTCTTTTGGCAATGTGAGGGCCCGGAAACCTGGCCCTGTCTTCTTG
ACGAGCATTCCTAGGGGTCTTTCCCCTCTCGCCAAAGGAATGCAAGGTCTGTTGAATGTCGTGA
AGGAAGCAGTTCCTCTGGAAGCTTCTTGAAGACAAACAACGTCTGTAGCGACCCTTTGCAGGCA
GCGGAACCCCCACCTGGCGACAGGTGCCTCTGCGGCCAAAAGCCACGTGTATAAGATACACCT
GCAAAGGCGGCACAACCCCAGTGCCACGTTGTGAGTTGGATAGTTGTGGAAAGAGTCAAATGGC
TCTCCTCAAGCGTATTCAACAAGGGGCTGAAGGATGCCCAGAAGGTACCCCATTGTATGGGATC
TGATCTGGGGCCTCGGTGCACATGCTTTACATGTGTTTAGTCGAGGTTAAAAAAACGTCTAGGC
```

Figure 9 (Continued)

```
CCCCCGAACCACGGGGACGTGGTTTTCCTTTGAAAAACACGATGATAATATGGCCACAACCATG
GTGAGCAAGGGCGAGGAGCTGTTCACCGGGGTGGTGCCCATCCTGGTCGAGCTGGACGGCGACG
TAAACGGCCACAAGTTCAGCGTGTCCGGCGAGGGCGAGGGCGATGCCACCTACGGCAAGCTGAC
CCTGAAGTTCATCTGCACCACCGGCAAGCTGCCCGTGCCCTGGCCCACCCTCGTGACCACCCTG
ACCTACGGCGTGCAGTGCTTCAGCCGCTACCCCGACCACATGAAGCAGCACGACTTCTTCAAGT
CCGCCATGCCCGAAGGCTACGTCCAGGAGCGCACCATCTTCTTCAAGGACGACGGCAACTACAA
GACCCGCGCCGAGGTGAAGTTCGAGGGCGACACCCTGGTGAACCGCATCGAGCTGAAGGGCATC
GACTTCAAGGAGGACGGCAACATCCTGGGGCACAAGCTGGAGTACAACTACAACAGCCACAACG
TCTATATCATGGCCGACAAGCAGAAGAACGGCATCAAGGTGAACTTCAAGATCCGCCACAACAT
CGAGGACGGCAGCGTGCAGCTCGCCGACCACTACCAGCAGAACACCCCCATCGGCGACGGCCCC
GTGCTGCTGCCCGACAACCACTACCTGAGCACCCAGTCCGCCCTGAGCAAAGACCCCAACGAGA
AGCGCGATCACATGGTCCTGCTGGAGTTCGTGACCGCCGCGGGATCACTCTCGGCATGGACGA
GCTGTACAAGTAAAGCGGCCGCGATCTTTTTCCCTCTGCCAAAAATTATGGGGACATCATGAAG
CCCCTTGAGCATCTGACTTCTGGCTAATAAAGGAAATTTATTTTCATTGCAATAGTGTGTTGGA
ATTTTTTGTGTCTCTCACTCGGAAGGACATATGGGAGGGCAAATCATTTAAAACATCAGAATGA
GTATTTGGTTTAGAGTTTGGCAACATATGCCATATGCTGGCTGCCATGAACAAAGGTGGCTATA
AAGAGGTCATCAGTATATGAAACAGCCCCCTGCTGTCCATTCCTTATTCCATAGAAAAGCCTTG
ACTTGAGGTTAGATTTTTTTATATTTTGTTTTGTGTTATTTTTTTCTTTAACATCCCTAAAAT
TTTCCTTACATGTTTTACTAGCCAGATTTTTCCTCCTCTCCTGACTACTCCCAGTCATAGCTGT
CCCTCTTCTCTTATGAAGATCCCTCGACCTGCAGCCCAAGCTTGGCGTAATCATGGTCATAGCT
GTTTCCTGTGTGAAATTGTTATCCGCTCACAATTCCACACAACATACGAGCCGGAAGCATAAAG
TGTAAAGCCTGGGGTGCCTAATGAGTGAGCTAACTCACATTAATTGCGTTGCGCTCACTGCCCG
CTTTCCAGTCGGGAAACCTGTCGTGCCAGCGGATCCGCATCTCAATTAGTCAGCAACCATAGTC
CCGCCCCTAACTCCGCCCATCCCGCCCCTAACTCCGCCCAGTTCCGCCCATTCTCCGCCCATG
GCTGACTAATTTTTTTATTTATGCAGAGGCCGAGGCCGCCTAAACGGCCGGCCATcgataccg
tcgacctcgagggggggcccggtacccagcttttgttcccttagtgagggttaattgcgcgct
tggcgtaatcatggtcatagctgtttcctgtgtgaaattgttatccgctcacaattccacacaa
catacgagccggaagcataaagtgtaaagcctggggtgcctaatgagtgagctaactcacatta
attgcgttgcgctcactgcccgctttccagtcgggaaacctgtcgtgccagctgcattaatgaa
tcggccaacgcgcggggagaggcggtttgcgtattgggcgctcttccgcttcctcgctcactga
ctcgctgcgctcggtcgttcggctgcggcgagcggtatcagctcactcaaaggcggtaatacgg
ttatccacagaatcaggggataacgcaggaaagaacatgtgagcaaaaggccagcaaaaggcca
ggaaccgtaaaaaggccgcgttgctggcgttttccataggctccgcccccctgacgagcatca
caaaaatcgacgctcaagtcagaggtggcgaaacccgacaggactataaagataccaggcgttt
ccccctggaagctccctcgtgcgctctcctgttccgaccctgccgcttaccggatacctgtccg
cctttctcccttcgggaagcgtggcgctttctcatagctcacgctgtaggtatctcagttcggt
gtaggtcgttcgctccaagctgggctgtgcacgaaccccccgttcagcccgaccgctgcgcc
ttatccggtaactatcgtcttgagtccaacccggtaagacacgacttatcgccactggcagcag
ccactggtaacaggattagcagagcgaggtatgtaggcggtgctacagagttcttgaagtggtg
gcctaactacggctacactagaaggacagtatttggtatctgcgctctgctgaagccagttacc
ttcggaaaaagagttggtagctcttgatccggcaaacaaaccaccgctggtagcggtggttttt
ttgtttgcaagcagcagattacgcgcagaaaaaaaggatctcaagaagatcctttgatcttttc
```

Figure 9 (Continued)

```
tacggggtctgacgctcagtggaacgaaaactcacgttaagggattttggtcatgagattatca
aaaaggatcttcacctagatccttttaaattaaaaatgaagttttaaatcaatctaaagtatat
atgagtaaacttggtctgacagttaccaatgcttaatcagtgaggcacctatctcagcgatctg
tctatttcgttcatccatagttgcctgactcccgtcgtgtagataactacgatacggggagggc
ttaccatctggccccagtgctgcaatgataccgcgagacccacgctcaccggctccagatttat
cagcaataaaccagccagccggaagggccgagcgcagaagtggtcctgcaactttatccgcctc
catccagtctattaattgttgccgggaagctagagtaagtagttcgccagttaatagtttgcgc
aacgttgttgccattgctacaggcatcgtggtgtcacgctcgtcgtttggtatggcttcattca
gctccggttcccaacgatcaaggcgagttacatgatccccatgttgtgcaaaaaagcggttag
ctccttcggtcctccgatcgttgtcagaagtaagttggccgcagtgttatcactcatggttatg
gcagcactgcataattctcttactgtcatgccatccgtaagatgcttttctgtgactggtgagt
actcaaccaagtcattctgagaatagtgtatgcggcgaccgagttgctcttgccggcgtcaat
acgggataataccgcgccacatagcagaactttaaaagtgctcatcattggaaaacgttcttcg
gggcgaaaactctcaaggatcttaccgctgttgagatccagttcgatgtaacccactcgtgcac
ccaactgatcttcagcatcttttactttcaccagcgtttctggtgagcaaaaacaggaaggca
aaatgccgcaaaaaagggaataagggcgacacggaaatgttgaatactcatactcttccttttt
caatattattgaagcatttatcagggttattgtctcatgagcggatacatatttgaatgtattt
agaaaaataaacaaatagggggttccgcgcacatttccccgaaaagtgccac    (SEQ ID
NO:1)
```

Figure 10 ctaaattgtaagcgttaatatttttgttaaaattcgcgttaaatttttgttaaatcagctcattt
tttaaccaataggccgaaatcggcaaaatcccttataaatcaaaagaatagaccgagatagggt
tgagtg  (SEQ ID NO:2)

F1 ori:
ttgttccagtttggaacaagagtccactattaaagaacgtggactccaacgtcaaagggcgaaa
aaccgtctatcagggcgatggcccactacgtgaaccatcaccctaatcaagttttttggggtcg
aggtgccgtaaagcactaaatcggaaccctaaagggagccccgatttagagcttgacggggaa
agccggcgaacgtggcgagaaaggaagggaagaaagcgaaaggagcgggcgctagggcgctggc
aagtgtagcggtcacgctgcgcgtaaccaccacacccgccgcgcttaatgcgccgctacagggc
gcgtc  (SEQ ID NO:3)

LacZ alpha:
ccattcgccattcaggctgcgcaactgttgggaagggcgatcggtgcggcctcttcgctatta
cgccagctggcgaaaggggggatgtgctgcaaggcgattaagttgggtaacgccagggttttccc
agtcacgacgt  (SEQ ID NO:4)

M13 fwd:
tgtaaaacgacggccagtgagcgcgc  (SEQ ID NO:5)

T7:
gtaatacgactcactatagggcgaattggagctccaccgcggtggcggccgctctagaactagt
g  (SEQ ID NO:6)

BAMH1, p16 promoter:
GATCC  (SEQ ID NO:7)

forprimer3, p16 promoter:
GTGTAAAGTCACT  (SEQ ID NO:8)

Figure 10 (Continued)

```
p16 promoter:
CTTTTATAGCTACATCTGCATAGATCCCCTGTATGAAAGCATGTACTACCTGGATAATAATATC
TGTATTTTTCTGTAGTAGGAAATCAGTGTAGTTTTTAAAACCAAAAAGTATTGTTATTAATCTA
TCTTTGATCTCAAACAATTTCAATGACCTAGTATAGTGATTTCTACGGAAAGCCCTGCAATTTA
CTCAAAGCAGTTTTTAAATATTGTTTTAAAAGTGTGTGTGTGTGTGTGTGTGTGTGTGTGTGTG
TGTGTGGTGTTAAAGTCATTTTCAAACCCCTCACAATGTCTTGAATGTGACATTTGAGTCATTT
ATGGTAACTTATAACTCCTTTGAAGAAGTTATTCAGAATTGAGGTTCCAGACACACAAATGCAC
AATACACCATTTTTCCTTCCAGTTAACAATCAGAGGGCAACACTTATTTTTAAAGGAAAATCGA
CTCCATAAGGGACTTTATAAAGGGGTAGACATAAACCAGTATCAGGGATAAACTCTCCGTTCCC
CTGTTTAACCTAATTTTCCCAGGGCCATCCTGGAATACGAATTTTCTCTTGAAATACAGTCAAA
GAAAAAGTGGTAGGCTACAGAGCAGAGGAAACACTGGACACAGCGACCCACCCCAGAGTCACTT
CCCTTAATCTAATGACTAGGTTTTTTCTGAAAGTTATTTTGTTAGAACACAGGAACTTTTGCGA
CCACAGTGATGCTTTTAGAGGGTTGAATCCTCAAAAAGAAAATTAATCGCAACTAGTAGAAGGG
AGATTACTTATTGATTCTTATAACTTCTGCAGGAATACACAGTTATGAGTTAGGGCAAAGAGAA
AATTGACTTTTAATATTCTCTATCACTAACATGAGAGAACATGTATGTGTTCCAAAATAATTTT
TATTTATTGAAAACCCGCTATATACCTGGATTTTCACAGAATATTCATTACTCTCCAAAATGGC
CTTTTCTAGGTGAATTTTATTTTCCTTACAGACCTCAAGAAGTTTACATAATTTACTTAAACCT
GAGGAGAGAGAACAAAGCCTCAGAAAATTTACATAGTTTATTTAAACTAAACTCAGCTTGCTTG
GTAGCAGCTTCTAATCCCAGCAGTTAAAGAGACAGAAGCAGGGCCAACCTGGGGTATAATATAA
GGTGAGACTCTCCTTTCTTTCTCTCTGTCTCTGTCTGTCTCTGTCTCTGTGTGTGTGTGTGTGT
GTGTGTGTGTGTGTGTGTCTCCTCTCTCTCTCTCTCTCTCTCTCTCTCTCTCTCTCTCTGTCTC
TCTCTCCCTCCCCCTCCCTCCCTCTCCCCCTCCTCTCTCCCTCCCTCTCCCTCCCCCCCCCCCA
CACATTTGAATTCGTGGAGTTGGTAAATGAGGGGTCAGTTCTCTGTCTGTCTGTAGTTTTGTGT
CCACAGGATATGACTGACATTCTCACCACACACATACAAAGTCAAAAATAGCTGTGGCCATATA
AAGAATATGGGGAGAGAAAATTATTCAAAATCTGCAGAAAATAATGCCAGGCCTTTAATCCTGG
CACCCAGGAGGCAGAAGGGAGACAGAGTTCTGAGTTTATGCTGAGTTCCAGGAGTGGAAGAAAG
GGCCATTGCCTTTCTGGTGAGGACTGTCTTTTTAAATCCTCCCTTCTGTCCAGTACTGGTAACT
CTGCCCAAAGCGTGTTCTTCTTCCTGCCTCACAAGATTGCAAAGACGTTTTTAACGAACAATTT
AAACCGGTGCAACGTTTATGCGCAGCACACCAACTCATTTAAACAAACAACAGCCCCATAAAAT
AGAAATACTTTATAAGCAGATTGCCCTCCGATGACTTCACCCCGTCACTTTTTTATAGTTGTGT
ACAGAATCCTAGCACTGATACAGCAACATCAGAAATGTTTCTGCAAATCCTTCGCAAAGATTCG
GATTTCATACTGGGCGTGGTACCCTCCAAAATGAGTTGTTTGAGCTAGGGTTGTTGGGATCTCA
GCTTGGCGAAGTTGTAGCTCTTTCTTCTGAATAAAGATGACACAATTTCTGCTAAGATGTTA
AATACCTTAAGTTTCAGTGTAGTGATGAAAATTACCCTCCTTCGTTTTCTAATACCTGGGTGT
TGCACTGGGGAGGAAGGAGAGATTTCGAGAAGGACTAGTTCACTTTCTCAGAAGACACGTGTGC
ACTTCTTTGCTGTGCGGGTCCAGAAGGAGCCCAGCGTGTCAAAGGGTGACCAGGCATGGGGGAG
GGGTGTTAGCGTGGGTAGCAGGCGGGGCTGTCCGATCCTTTAGCGCTGTTTCAACGCCCAGCT
CTCCTCCTGAACCCTGCATCTCTTCTGTAGTCCGGGCTCCATCCCTTTCCCCTCCCCATCCGG
AGGTGGGGGGAACAGCAGTGTTTTCAGGGGTGTTCAATTCATGCTATATTCAGGGCAAATAGCG
CCACCTATGGCGGGCTGTGGAGCCAGGTCAGGAGCAGAGTGTGGCTCCCCCCCCCCCCCACACC
ATCCTCAGAGGAAGGAAGGAGGGACCCACTGGTCACACGACTGGGCGATTGGGCGGGCACTGAA
TCTCCGCGAGGAAAGCGAACTCGAGGAGAGCCATCACGCGTAGC    (SEQ ID NO:9)
```

Figure 10 (Continued)

FKBP:
atggggagtagcaagagcaagcctaaggaccccagccagcgctctagaggcgtccaagtcgaaa
ccattagtcccggcgatggcagaacatttcctaaaaggggacaaacatgtgtcgtccattatac
aggcatgttggaggacggcaaaaaggtggacagtagtagagatcgcaataaaccttcaaattc
atgttgggaaaacaagaagtcattaggggatgggaggagggcgtggctcaaatgtccgtcggcc
aacgcgctaagctcaccatcagccccgactacgcatacggcgctaccggacatcccggaattat
tcccctcacgctaccttggtgtttgacgtcgaactgttgaagctcgagactagaggagtgcag
gtggagactatctccccaggagacgggcgcaccttcccaagcgcggccagacctgcgtggtgc
actacaccgggatgcttgaagatggaaagaaagttgattcctcccgggacagaaacaagcccttt
taagtttatgctaggcaagcaggaggtgatccgaggctgggaagaagggttgcccagatgagt
gtgggtcagagagccaaactgactatatctccagattatgcctatggtgccactgggcacccag
gcatcatcccaccacatgccactctcgtcttcgatgtggagcttctaaaactggaaactagt
(SEQ ID NO:10)

Casp8:
agtgaatcacagactttggacaaagtttaccaaatgaaaagcaaacctcggggatactgtctga
tcatcaacaatcacaattttgcaaaagcacgggagaaagtgcccaaacttcacagcattaggga
caggaatggaacacacttggatgcaggggctttgaccacgacctttgaagagcttcattttgag
atcaagccccacgatgactgcacagtagagcaaatctatgagattttgaaaatctaccaactca
tggaccacagtaacatggactgcttcatctgctgtatcctctcccatggagacaagggcatcat
ctatggcactgatggacaggaggcccccatctatgagctgacatctcagttcactggtttgaag
tgcccttcccttgctggaaaacccaaagtgttttttattcaggcttgtcaggggataactacc
agaaaggtatacctgttgagactgattcagaggagcaaccctatttagaaatggatttatcatc
acctcaaacgagatatatcccggatgaggctgactttctgctggggatggccactgtgataac
tgtgtttcctaccgaaaccctgcagagggaacctggtacatccagtcactttgccagagcctga
gagagcgatgtcctcgaggcgatgatattctcaccatcctgactgaagtgaactatgaagtaag
caacaaggatgacaagaaaaacatggggaaacagatgcctcagcctactttcacactaagaaaa
aaacttgtcttcccttctgat (SEQ ID NO:11)

Flag/Tag/Stop:
Gattacaaggatgacgacgataagtga (SEQ ID NO:12)

3'UTR:
ggatc (SEQ ID NO:13)

Multiple cloning site (MluI, PacI, XhoI, PmeI)
aacctcgaggaattcACGCGTTTAATTAACTCGAGGTTT (SEQ ID NO:14)

Figure 10 (Continued)

```
IRES, GFP:
TCGAGGTCGACGGTATCGATAAGCTTGATATCGAATTCCGCCCCTCTCCCTCCCCCCCCCTAA
CGTTACTGGCCGAAGCCGCTTGGAATAAGGCCGGTGTGCGTTTGTCTATATGTTATTTTCCACC
ATATTGCCGTCTTTTGGCAATGTGAGGGCCCGGAAACCTGGCCCTGTCTTCTTGACGAGCATTC
CTAGGGGTCTTTCCCCTCTCGCCAAAGGAATGCAAGGTCTGTTGAATGTCGTGAAGGAAGCAGT
TCCTCTGGAAGCTTCTTGAAGACAAACAACGTCTGTAGCGACCCTTTGCAGGCAGCGGAACCCC
CCACCTGGCGACAGGTGCCTCTGCGGCCAAAAGCCACGTGTATAAGATACACCTGCAAAGGCGG
CACAACCCCAGTGCCACGTTGTGAGTTGGATAGTTGTGGAAAGAGTCAAATGGCTCTCCTCAAG
CGTATTCAACAAGGGGCTGAAGGATGCCCAGAAGGTACCCCATTGTATGGGATCTGATCTGGGG
CCTCGGTGCACATGCTTTACATGTGTTTAGTCGAGGTTAAAAAAACGTCTAGGCCCCCCGAACC
ACGGGGACGTGGTTTTCCTTTGAAAAACACGATGATAATATGGCCACAACCATGGTGAGCAAGG
GCGAGGAGCTGTTCACCGGGGTGGTGCCCATCCTGGTCGAGCTGGACGGCGACGTAAACGGCCA
CAAGTTCAGCGTGTCCGGCGAGGGCGAGGGCGATGCCACCTACGGCAAGCTGACCCTGAAGTTC
ATCTGCACCACCGGCAAGCTGCCCGTGCCCTGGCCCACCCTCGTGACCACCCTGACCTACGGCG
TGCAGTGCTTCAGCCGCTACCCCGACCACATGAAGCAGCACGACTTCTTCAAGTCCGCCATGCC
CGAAGGCTACGTCCAGGAGCGCACCATCTTCTTCAAGGACGACGGCAACTACAAGACCCGCGCC
GAGGTGAAGTTCGAGGGCGACACCCTGGTGAACCGCATCGAGCTGAAGGGCATCGACTTCAAGG
AGGACGGCAACATCCTGGGGCACAAGCTGGAGTACAACTACAACAGCCACAACGTCTATATCAT
GGCCGACAAGCAGAAGAACGGCATCAAGGTGAACTTCAAGATCCGCCACAACATCGAGGACGGC
AGCGTGCAGCTCGCCGACCACTACCAGCAGAACACCCCCATCGGCGACGGCCCCGTGCTGCTGC
CCGACAACCACTACCTGAGCACCCAGTCCGCCCTGAGCAAAGACCCCAACGA    (SEQ ID
NO:15)

Rabbit B-globin PA:
GAAGCGCGATCACATGGTCCTGCTGGAGTTCGTGACCGCCGCCGGGATCACTCTCGGCATGGAC
GAGCTGTACAAGTAAAGCGGCCGCGATCTTTTTCCCTCTGCCAAAAATTATGGGGACATCATGA
AGCCCCTTGAGCATCTGACTTCTGGCTAATAAAGGAAATTTATTTTCATTGCAATAGTGTGTTG
GAATTTTTTGTGTCTCTCACTCGGAAGGACATATGGGAGGGCAAATCATTTAAAACATCAGAAT
GAGTATTTGGTTTAGAGTTTGGCAACATATGCCATATGCTGGCTGCCATGAACAAAGGTGGCTA
TAAAGAGGTCATCAGTATATGAAACAGCCCCCTGCTGTCCATTCCTTATTCCATAGAAAGCCT
TGACTTGAGGTTAGATTTTTTTATATTTGTTTTGTGTTATTTTTTCTTTAACATCCCTAAA
ATTTTCCTTACATGTTTTACTAGCCAGATTTTTCCTCCTCTCCTGACTACTCCCAGTCATAGCT
GTCCCTCTTCTCTTATGAAGATCCCTCGACCTGCAGCCCAAGCTTGGCGTAAT   (SEQ ID
NO:16)

M13-rev:
CATGGTCATAGCTGTTTCCTGTGTGA   (SEQ ID NO:17)
```

Figure 10 (Continued)

```
LacO:
AATTGTTATCCGCTCACAATTCCACACAACATACGAGCCGGAAGCATAAAGTGTAAAGCCTGGG
GTGCCTAATGAGTGAGCTAACTCACATTAATTGCGTTGCGCTCACTGCCCGCTTTCCAGTCGGG
AAACCTGTCGTGCCAGCGGATCCGCATCTCAATTAGTCAGCAACCATAGTCCCGCCCCTAACTC
CGCCCATCCCGCCCCTAACTCCGCCCAGTTCCGCCCATTCTCCGCCCCATGGCTGACTAATTTT
TTTTATTTATGCAGAGGCCGAGGCCGCCT    (SEQ ID NO:18)

FseI, linker:
AAACGGCCGGCCATcgataccgtcgacctcgagggggggcccggtacccagcttttgt    (SEQ
ID NO:19)

T3:
Tccctttagtgagggttaattgcgcgcttggcgtaat    (SEQ ID NO:20)

M13-rev:
Catggtcatagctgtttcctgtgtga    (SEQ ID NO:21)

LacO:
Aattgttatccgctcacaattccacacaacatacgagccggaagcataaagtgtaaagcctggg
gtgcctaatgagtgagctaactcacattaattgcgttgcgctcactgcccgctttccagtcggg
aaacctgtcgtgccagctgcattaatgaatcggccaacgcgcggggagaggcggtttgcgtatt
gggcgctcttccgcttcctcgctcactgactcgctgcgctcggtcgttcggctgcggcgagcgg
tatcagctcactcaaaggcggtaatacggttatccacagaatcaggggataacgcaggaaagaa
catgtgagcaaaaggccagcaaaaggccaggaaccgtaaaaa    (SEQ ID NO:22)

ColE1 origin:
Ggccgcgttgctggcgtttttccataggctccgcccccctgacgagcatcacaaaaatcgacgc
tcaagtcagaggtggcgaaacccgacaggactataaagataccaggcgtttccccctggaagct
ccctcgtgcgctctcctgttccgaccctgccgcttaccggatacctgtccgcctttctccctc
gggaagcgtggcgctttctcatagctcacgctgtaggtatctcagttcggtgtaggtcgttcgc
tccaagctgggctgtgtgcacgaaccccccgttcagcccgaccgctgcgccttatccggtaact
atcgtcttgagtccaacccggtaagacacgacttatcgccactggcagcagccactggtaacag
gattagcagagcgaggtatgtaggcggtgctacagagttcttgaagtggtggcctaactacggc
tacactagaaggacagtatttggtatctgcgctctgctgaagccagttaccttcggaaaaagag
ttggtagctcttgatccggcaaacaaaccaccgctggtagcggtggtttttttgtttgcaagca
gcagattacgcgcagaaaaaaaggatctcaagaagatcctttgatcttttctacggggtctgac
gctcagtggaacgaaaactcacgttaagggattttggtcatgagattatcaaaaaggatcttca
cctagatccttttaaattaaaaatgaagttttaaatcaatctaaagtatatatgagtaaacttg
gtctgacagtta    (SEQ ID NO:23)
```

Figure 10 (Continued)

AmpR:
Ccaatgcttaatcagtgaggcacctatctcagcgatctgtctatttcgttcatccatagttgcc
tgactccccgtcgtgtagataactacgatacgggagggcttaccatctggccccagtgctgcaa
tgatacccgcgagacccacgctcaccggctccagatttatcagcaataaaccagccagccggaag
ggccgagcgcagaagtggtcctgcaactttatccgcctccatccagtctattaattgttgccgg
gaagctagagtaagtagttcgccagttaatagtttgcgcaacgttgttgccattgctacaggca
tcgtggtgtcacgctcgtcgtttggtatggcttcattcagctccggttcccaacgatcaaggcg
agttacatgatccccatgttgtgcaaaaagcggttagctccttcggtcctccgatcgttgtc
agaagtaagttggccgcagtgttatcactcatggttatggcagcactgcataattctcttactg
tcatgccatccgtaagatgcttttctgtgactggtgagtactcaaccaagtcattctgagaata
gtgtatgcggcgaccgagttgctcttgcccggcgtcaatacgggataataccgcgccacatagc
agaactttaaaagtgctcatcattggaaaacgttcttcggggcgaaaactctcaaggatcttac
cgctgttgagatccagttcgatgtaacccactcgtgcacccaactgatcttcagcatcttttac
tttcaccagcgtttctgggtgagcaaaaacaggaaggcaaaatgccgcaaaaaagggaataagg
gcgacacggaaatgttgaatactcatactcttccttttcaatattattgaagcatttatcagg
gttattgtctcatgagcggatacatatttgaatgtatttagaaaaataaacaatagggttcc
gcgcacatttccccgaaaagtgccac    (SEQ ID NO:24)

SEQUENCE LISTING

<160> NUMBER OF SEQ ID NOS: 28

<210> SEQ ID NO 1
<211> LENGTH: 9267
<212> TYPE: DNA
<213> ORGANISM: Artificial Sequence
<220> FEATURE:
<223> OTHER INFORMATION: pBLUESCRIPT II KS vector + construct

<400> SEQUENCE: 1

| | | | | | |
|---|---|---|---|---|---|
| ctaaattgta | agcgttaata | ttttgttaaa | attcgcgtta | aattttttgtt | aaatcagctc | 60 |
| attttttaac | caataggccg | aaatcggcaa | aatcccttat | aaatcaaaag | aatagaccga | 120 |
| gatagggttg | agtgttgttc | cagtttggaa | caagagtcca | ctattaaaga | acgtggactc | 180 |
| caacgtcaaa | gggcgaaaaa | ccgtctatca | gggcgatggc | ccactacgtg | aaccatcacc | 240 |
| ctaatcaagt | tttttggggt | cgaggtgccg | taaagcacta | aatcggaacc | ctaaagggag | 300 |
| cccccgattt | agagcttgac | ggggaaagcc | ggcgaacgtg | gcgagaaagg | aagggaagaa | 360 |
| agcgaaagga | gcgggcgcta | gggcgctggc | aagtgtagcg | gtcacgctgc | gcgtaaccac | 420 |
| cacacccgcc | gcgcttaatg | cgccgctaca | gggcgcgtcc | cattcgccat | tcaggctgcg | 480 |
| caactgttgg | aagggcgat | cggtgcgggc | ctcttcgcta | ttacgccagc | tggcgaaagg | 540 |
| gggatgtgct | gcaaggcgat | taagttgggt | aacgccaggg | ttttcccagt | cacgacgttg | 600 |
| taaaacgacg | gccagtgagc | gcgcgtaata | cgactcacta | tagggcgaat | tggagctcca | 660 |
| ccgcggtggc | ggccgctcta | gaactagtgg | atccgtgtaa | agtcactgct | tttatagcta | 720 |
| catctgcata | gatcccctgt | atgaaagcat | gtactacctg | gataataata | tctgtatttt | 780 |
| tctgtagtag | gaaatcagtg | tagttttttaa | aaccaaaaag | tattgttatt | aatctatctt | 840 |
| tgatctcaaa | caatttcaat | gacctagtat | agtgatttct | acggaaagcc | ctgcaattta | 900 |
| ctcaaagcag | tttttaaata | ttgttttaaa | agtgtgtgtg | tgtgtgtgtg | tgtgtgtgtg | 960 |
| tgtgtgtgtg | gtgttaaagt | cattttcaaa | ccctcacaa | tgtcttgaat | gtgacatttg | 1020 |
| agtcattat | ggtaacttat | aactccttg | aagaagttat | tcagaattga | ggttccagac | 1080 |
| acacaaatgc | acaatacacc | attttttcctt | ccagttaaca | atcagagggc | aacacttatt | 1140 |
| tttaaaggaa | aatcgactcc | ataagggact | ttataaaggg | gtagacataa | accagtatca | 1200 |
| gggataaaact | ctccgttccc | ctgtttaacc | taattttccc | agggccatcc | tggaatacga | 1260 |
| attttctctt | gaaatacagt | caaagaaaaa | gtggtaggct | acagagcaga | ggaaacactg | 1320 |
| gacacagcga | cccaccccag | agtcacttcc | cttaatctaa | tgactaggtt | ttttctgaaa | 1380 |
| gttattttgt | tagaacacag | gaacttttgc | gaccacagtg | atgcttttag | agggttgaat | 1440 |
| cctcaaaaag | aaaattaatc | gcaactagta | gaagggagat | tacttattga | ttcttataac | 1500 |
| ttctgcagga | atacacagtt | atgagttagg | gcaaagagaa | aattgacttt | taatattctc | 1560 |
| tatcactaac | atgagagaac | atgtatgtgt | tccaaaataa | tttttattta | ttgaaaaccc | 1620 |
| gctatatacc | tggattttca | cagaatattc | attactctcc | aaaatggcct | tttctaggtg | 1680 |
| aattttattt | tccttacaga | cctcaagaag | tttacataat | ttacttaaac | ctgaggagag | 1740 |
| agaacaaagc | ctcagaaaat | ttacatagtt | tatttaaact | aaactcagct | tgcttggtag | 1800 |
| cagcttctaa | tcccagcagt | taaagagaca | gaagcagggc | caacctgggg | tataatataa | 1860 |
| ggtgagactc | tccttttcttt | ctctctgtct | ctgtctgtct | ctgtctctgt | gtgtgtgtgt | 1920 |
| gtgtgtgtgt | gtgtgtgtgt | gtgtctcctc | tctctctctc | tctctctctc | tctctctctc | 1980 |
| tctgtctctc | tctccctccc | cctccctccc | tctccccctc | ctctctccct | ccctctccct | 2040 |

-continued

```
cccccccccc cacacatttg aattcgtgga gttggtaaat gagggtcag ttctctgtct     2100 gtctgtagtt ttgtgtccac aggatatgac tgacattctc accacacaca tacaaagtca     2160
aaaatagctg tggccatata agaatatgg ggagagaaaa ttattcaaaa tctgcagaaa      2220
ataatgccag gcctttaatc ctggcaccca ggaggcagaa gggagacaga gttctgagtt     2280
tatgctgagt tccaggagtg aagaaaggg ccattgcctt tctggtgagg actgtctttt      2340
taaatcctcc cttctgtcca gtactggtaa ctctgcccaa agcgtgttct tcttcctgcc     2400
tcacaagatt gcaaagacgt ttttaacgaa caatttaaac cggtgcaacg tttatgcgca     2460
gcacaccaac tcatttaaac aaacaacagc cccataaaat agaaatactt tataagcaga     2520
ttgccctccg atgacttcac cccgtcactt ttttatagtt gtgtacagaa tcctagcact     2580
gatacagcaa catcagaaat gtttctgcaa atccttcgca aagattcgga tttcatactg     2640
ggcgtggtac cctccaaaat gagttgtttg agctagggtt gttgggatct cagcttggcg     2700
aagttgtagc tctttcttct gaataaaaga tgacacaatt ttctgctaag atgttaaata     2760
ccttaagttt cagtgtagtg atgaaaatta ccctccttcg ttttctaat acctgggtgt      2820 tgcactgggg aggaaggaga gatttcgaga aggactagtt cactttctca gaagacacgt     2880
gtgcacttct ttgctgtgcg ggtccagaag gagcccagcg tgtcaaaggg tgaccaggca     2940
tgggggaggg gtgttagcgt gggtagcagg cggggctgt ccgatccttt agcgctgttt      3000
caacgcccag ctctcctcct gaaccctgca tctcttctgt agtccgggct ccatcccttt     3060
cccctccccc atccggaggt gggggaaca gcagtgtttt caggggtgtt caattcatgc      3120
tatattcagg gcaaatagcg ccacctatgg cgggctgtgg agccaggtca ggagcagagt     3180
gtggctcccc ccccccccca caccatcctc agaggaagga aggagggacc cactggtcac     3240
acgactgggc gattgggcgg gcactgaatc tccgcgagga aagcgaactc gaggagagcc     3300
atcacgcgta gcatggggag tagcaagagc aagcctaagg accccagcca gcgctctaga     3360
ggcgtccaag tcgaaaccat tagtcccggc gatggcagaa catttcctaa aaggggacaa     3420
acatgtgtcg tccattatac aggcatgttg gaggacggca aaaaggtgga cagtagtaga     3480
gatcgcaata aaccttttcaa attcatgttg ggaaaacaag aagtcattag gggatgggag    3540
gagggcgtgg ctcaaatgtc cgtcggccaa cgcgctaagc tcaccatcag ccccgactac     3600
gcatacggcg ctaccggaca tcccggaatt attccccctc acgctacctt ggtgtttgac     3660
gtcgaactgt tgaagctcga gactagagga gtgcaggtgg agactatctc cccaggagac     3720
gggcgcacct tccccaagcg cggccagacc tgcgtggtgc actacaccgg gatgcttgaa     3780
gatggaaaga aagttgattc ctcccgggac agaaacaagc cctttaagtt tatgctaggc     3840
aagcaggagg tgatccgagg ctgggaagaa ggggttgccc agatgagtgt gggtcagaga     3900
gccaaactga ctatatctcc agattatgcc tatggtgcca ctgggcaccc aggcatcatc     3960
ccaccacatg ccactctcgt cttcgatgtg gagcttctaa aactgaaaac tagtagtgaa     4020
tcacagactt tggacaaagt ttaccaaatg aaaagcaaac ctcggggata ctgtctgatc     4080
atcaacaatc acaattttgc aaaagcacgg gagaaagtgc ccaaacttca cagcattagg     4140
gacaggaatg gaacacactt ggatgcaggg gctttgacca cgacctttga agagcttcat     4200
tttgagatca gccccacga tgactgcaca gtagagcaaa tctatgagat tttgaaaatc      4260
taccaactca tggaccacag taacatggac tgcttcatct gctgtatcct ctcccatgga     4320
gacaagggca tcatctatgg cactgatgga caggaggccc ccatctatga gctgacatct     4380
```

```
cagttcactg gtttgaagtg cccttcccct gctggaaaac ccaaagtgtt ttttattcag    4440
gcttgtcagg gggataacta ccagaaaggt atacctgttg agactgattc agaggagcaa    4500
ccctatttag aaatggattt atcatcacct caaacgagat atatcccgga tgaggctgac    4560
tttctgctgg ggatgccac tgtgaataac tgtgtttcct accgaaaccc tgcagaggga    4620
acctggtaca tccagtcact ttgccagagc ctgagagagc gatgtcctcg aggcgatgat    4680
attctcacca tcctgactga agtgaactat aagtaagca acaaggatga caagaaaaac    4740
atggggaaac agatgcctca gcctactttc acactaagaa aaaaacttgt cttcccttct    4800
gatgattaca aggatgacga cgataagtga ggatcaacct cgaggaattc acgcgtttaa    4860
ttaactcgag gttttcgagg tcgacggtat cgataagctt gatatcgaat tccgcccctc    4920
tccctccccc cccctaacg ttactggccg aagccgcttg gaataaggcc ggtgtgcgtt    4980
tgtctatatg ttattttcca ccatattgcc gtcttttggc aatgtgaggg cccggaaacc    5040
tggccctgtc ttcttgacga gcattcctag gggtctttcc cctctcgcca aggaatgca    5100 aggtctgttg aatgtcgtga aggaagcagt tcctctggaa gcttcttgaa gacaaacaac    5160
gtctgtagcg accctttgca ggcagcggaa ccccccacct ggcgacaggt gcctctgcgg    5220
ccaaaagcca cgtgtataag atacacctgc aaaggcggca caaccccagt gccacgttgt    5280
gagttggata ttgtggaaa gagtcaaatg gctctcctca agcgtattca acaaggggct    5340
gaaggatgcc cagaaggtac cccattgtat gggatctgat ctgggcctc ggtgcacatg    5400 ctttacatgt gtttagtcga ggttaaaaaa acgtctaggc ccccgaacc acggggacgt    5460 ggttttcctt tgaaaaacac gatgataata tggccacaac catggtgagc aagggcgagg    5520
agctgttcac cggggtggtg cccatcctgg tcgagctgga cggcgacgta acggccaca    5580 agttcagcgt gtccggcgag ggcgagggcg atgccaccta cggcaagctg accctgaagt    5640
tcatctgcac caccggcaag ctgcccgtgc cctggcccac cctcgtgacc accctgacct    5700
acggcgtgca gtgcttcagc cgctaccccg accacatgaa gcagcacgac ttcttcaagt    5760
ccgccatgcc cgaaggctac gtccaggagc gcaccatctt cttcaaggac gacggcaact    5820
acaagacccg cgccgaggtg aagttcgagg gcgacaccct ggtgaaccgc atcgagctga    5880
agggcatcga cttcaaggag gacggcaaca tcctggggca caagctggag tacaactaca    5940
acagccacaa cgtctatatc atggccgaca agcagaagaa cggcatcaag gtgaacttca    6000
agatccgcca caacatcgag gacggcagcg tgcagctcgc cgaccactac cagcagaaca    6060
cccccatcgg cgacggcccc gtgctgctgc ccgacaacca ctacctgagc acccagtccg    6120
ccctgagcaa agaccccaac gagaagcgcg atcacatggt cctgctggag ttcgtgaccg    6180
ccgccgggat cactctcggc atggacgagc tgtacaagta aagcggccgc gatctttttc    6240
cctctgccaa aaattatggg gacatcatga agccccttga gcatctgact tctggctaat    6300
aaaggaaatt tattttcatt gcaatagtgt gttggaattt tttgtgtctc tcactcggaa    6360
ggacatatgg gagggcaaat catttaaaac atcagaatga gtatttggtt tagagtttgg    6420
caacatatgc catatgctgg ctgccatgaa caaaggtggc tataaagagg tcatcagtat    6480
atgaaacagc cccctgctgt ccattcctta ttccatagaa aagccttgac ttgaggttag    6540
atttttttta tattttgttt tgtgttattt ttttctttaa catccctaaa attttcctta    6600
catgttttac tagccagatt tttcctcctc tcctgactac tcccagtcat agctgtccct    6660
cttctcttat gaagatccct cgacctgcag cccaagcttg gcgtaatcat ggtcatagct    6720
gtttcctgtg tgaaattgtt atccgctcac aattccacac aacatacgag ccggaagcat    6780
```

```
aaagtgtaaa gcctggggtg cctaatgagt gagctaactc acattaattg cgttgcgctc    6840
actgcccgct ttccagtcgg gaaacctgtc gtgccagcgg atccgcatct caattagtca    6900
gcaaccatag tcccgcccct aactccgccc atcccgcccc taactccgcc cagttccgcc    6960
cattctccgc cccatggctg actaattttt tttatttatg cagaggccga ggccgcctaa    7020
acggccggcc atcgataccg tcgacctcga gggggggccc ggtacccagc ttttgttccc    7080
tttagtgagg gttaattgcg cgcttggcgt aatcatggtc atagctgttt cctgtgtgaa    7140
attgttatcc gctcacaatt ccacacaaca tacgagccgg aagcataaag tgtaaagcct    7200
ggggtgccta atgagtgagc taactcacat taattgcgtt gcgctcactg cccgctttcc    7260
agtcgggaaa cctgtcgtgc cagctgcatt aatgaatcgg ccaacgcgcg gggagaggcg    7320
gtttgcgtat tgggcgctct tccgcttcct cgctcactga ctcgctgcgc tcggtcgttc    7380
ggctgcggcg agcggtatca gctcactcaa aggcggtaat acggttatcc acagaatcag    7440
gggataacgc aggaaagaac atgtgagcaa aaggccagca aaaggccagg aaccgtaaaa    7500
aggccgcgtt gctggcgttt ttccataggc tccgcccccc tgacgagcat cacaaaaatc    7560
gacgctcaag tcagaggtgg cgaaacccga caggactata aagataccag gcgtttcccc    7620
ctggaagctc cctcgtgcgc tctcctgttc cgaccctgcc gcttaccgga tacctgtccg    7680
cctttctccc ttcgggaagc gtggcgcttt ctcatagctc acgctgtagg tatctcagtt    7740
cggtgtaggt cgttcgctcc aagctgggct gtgtgcacga accccccgtt cagcccgacc    7800
gctgcgcctt atccggtaac tatcgtcttg agtccaaccc ggtaagacac gacttatcgc    7860
cactggcagc agccactggt aacaggatta gcagagcgag gtatgtaggc ggtgctacag    7920
agttcttgaa gtggtggcct aactacggct acactagaag gacagtattt ggtatctgcg    7980
ctctgctgaa gccagttacc ttcggaaaaa gagttggtag ctcttgatcc ggcaaacaaa    8040
ccaccgctgg tagcggtggt ttttttgttt gcaagcagca gattacgcgc agaaaaaaag    8100
gatctcaaga agatcctttg atcttttcta cggggtctga cgctcagtgg aacgaaaact    8160
cacgttaagg gattttggtc atgagattat caaaaaggat cttcacctag atccttttaa    8220
attaaaaatg aagttttaaa tcaatctaaa gtatatatga gtaaacttgg tctgacagtt    8280
accaatgctt aatcagtgag gcacctatct cagcgatctg tctatttcgt tcatccatag    8340
ttgcctgact ccccgtcgtg tagataacta cgatacggga gggcttacca tctggcccca    8400
gtgctgcaat gataccgcga gacccacgct caccggctcc agatttatca gcaataaacc    8460
agccagccgg aagggccgag cgcagaagtg gtcctgcaac tttatccgcc tccatccagt    8520
ctattaattg ttgccgggaa gctagagtaa gtagttcgcc agttaatagt ttgcgcaacg    8580
ttgttgccat tgctacaggc atcgtggtgt cacgctcgtc gtttggtatg gcttcattca    8640
gctccggttc ccaacgatca aggcgagtta catgatcccc catgttgtgc aaaaaagcgg    8700
ttagctcctt cggtcctccg atcgttgtca gaagtaagtt ggccgcagtg ttatcactca    8760
tggttatggc agcactgcat aattctctta ctgtcatgcc atccgtaaga tgcttttctg    8820
tgactggtga gtactcaacc aagtcattct gagaatagtg tatgcggcga ccgagttgct    8880
cttgcccggc gtcaatacgg gataataccg cgccacatag cagaacttta aaagtgctca    8940
tcattggaaa acgttcttcg ggcgaaaac tctcaaggat cttaccgctg ttgagatcca    9000
gttcgatgta acccactcgt gcacccaact gatcttcagc atcttttact ttcaccagcg    9060
tttctgggtg agcaaaaaca ggaaggcaaa atgccgcaaa aaagggaata agggcgacac    9120
```

```
ggaaatgttg aatactcata ctcttccttt tcaatatta ttgaagcatt tatcagggtt    9180
attgtctcat gagcggatac atatttgaat gtatttagaa aaataaacaa atagggttc    9240 cgcgcacatt tccccgaaaa gtgccac                                       9267

<210> SEQ ID NO 2
<211> LENGTH: 134
<212> TYPE: DNA
<213> ORGANISM: Artificial Sequence
<220> FEATURE:
<223> OTHER INFORMATION: vector sequence

<400> SEQUENCE: 2
ctaaattgta agcgttaata ttttgttaaa attcgcgtta aattttttgtt aaatcagctc    60 attttttaac caataggccg aaatcggcaa aatcccttat aaatcaaaag aatagaccga   120
gatagggttg agtg                                                     134

<210> SEQ ID NO 3
<211> LENGTH: 325
<212> TYPE: DNA
<213> ORGANISM: Artificial Sequence
<220> FEATURE:
<223> OTHER INFORMATION: F1 phage

<400> SEQUENCE: 3
ttgttccagt ttggaacaag agtccactat taaagaacgt ggactccaac gtcaaagggc    60
gaaaaaccgt ctatcagggc gatggcccac tacgtgaacc atcaccctaa tcaagttttt   120
tggggtcgag gtgccgtaaa gcactaaatc ggaaccctaa agggagcccc cgatttagag   180
cttgacgggg aaagccggcg aacgtggcga aaaggaagg gaagaaagcg aaaggagcgg   240
gcgctagggc gctggcaagt gtagcggtca cgctgcgcgt aaccaccaca cccgccgcgc   300
ttaatgcgcc gctacagggc gcgtc                                         325

<210> SEQ ID NO 4
<211> LENGTH: 139
<212> TYPE: DNA
<213> ORGANISM: Escherichia coli

<400> SEQUENCE: 4
ccattcgcca ttcaggctgc gcaactgttg ggaagggcga tcggtgcggg cctcttcgct    60
attacgccag ctggcgaaag ggggatgtgc tgcaaggcga ttaagttggg taacgccagg   120
gttttcccag tcacgacgt                                                139

<210> SEQ ID NO 5
<211> LENGTH: 26
<212> TYPE: DNA
<213> ORGANISM: Artificial Sequence
<220> FEATURE:
<223> OTHER INFORMATION: M13 phage

<400> SEQUENCE: 5
tgtaaaacga cggccagtga gcgcgc                                        26

<210> SEQ ID NO 6
<211> LENGTH: 65
<212> TYPE: DNA
<213> ORGANISM: T7 phage

<400> SEQUENCE: 6
gtaatacgac tcactatagg gcgaattgga gctccaccgc ggtggcggcc gctctagaac    60
```

-continued

```
tagtg                                                              65

<210> SEQ ID NO 7
<211> LENGTH: 5
<212> TYPE: DNA
<213> ORGANISM: Artificial Sequence
<220> FEATURE:
<223> OTHER INFORMATION: BAMH1 site

<400> SEQUENCE: 7 gatcc                                                              5

<210> SEQ ID NO 8
<211> LENGTH: 13
<212> TYPE: DNA
<213> ORGANISM: Artificial Sequence
<220> FEATURE:
<223> OTHER INFORMATION: Forprimer3 site

<400> SEQUENCE: 8
gtgtaaagtc act                                                     13

<210> SEQ ID NO 9
<211> LENGTH: 2604
<212> TYPE: DNA
<213> ORGANISM: Mus musculus

<400> SEQUENCE: 9
cttttatagc tacatctgca tagatcccct gtatgaaagc atgtactacc tggataataa     60
tatctgtatt tttctgtagt aggaaatcag tgtagttttt aaaaccaaaa agtattgtta    120
ttaatctatc tttgatctca aacaatttca atgacctagt atagtgattt ctacggaaag    180
ccctgcaatt tactcaaagc agttttaaa tattgtttta aaagtgtgtg tgtgtgtgtg    240
tgtgtgtgtg tgtgtgtgtg tggtgttaaa gtcattttca aaccccctcac aatgtcttga    300 atgtgacatt tgagtcattt atggtaactt ataactcctt tgaagaagtt attcagaatt    360
gaggttccag acacacaaat gcacaataca ccattttttcc ttccagttaa caatcagagg    420
gcaacactta tttttaaagg aaaatcgact ccataaggga ctttataaag gggtagacat    480
aaaccagtat cagggataaa ctctccgttc ccctgtttaa cctaattttc ccagggccat    540
cctggaatac gaattttctc ttgaaataca gtcaaagaaa aagtggtagg ctacagagca    600
gaggaaacac tggacacagc gacccacccc agagtcactt cccttaatct aatgactagg    660
ttttttctga aagttatttt gttagaacac aggaactttt gcgaccacag tgatgctttt    720
agagggttga atcctcaaaa agaaaattaa tcgcaactag tagaagggag attacttatt    780
gattcttata acttctgcag gaatacacag ttatgagtta gggcaaagag aaaattgact    840
tttaatattc tctatcacta acatgagaga acatgtatgt gttccaaaat aattttttatt    900 tattgaaaac ccgctatata cctggatttt cacagaaat tcattactct ccaaaatggc    960
cttttctagg tgaattttat tttccttaca gacctcaaga agtttacata atttacttaa   1020
acctgaggag agagaacaaa gcctcagaaa atttacatag tttatttaaa ctaaactcag   1080
cttgcttggt agcagcttct aatcccagca gttaaagaga cagaagcagg gccaacctgg   1140
ggtataatat aaggtgagac tctcctttct ttctctctgt ctctgtctgt ctctgtctct   1200
gtgtgtgtgt gtgtgtgtgt gtgtgtgtgt gtgtgtctcc tctctctctc tctctctctc   1260
tctctctctc tctctgtctc tctctccctc ccctccctc cctctccccc tcctctctcc   1320
```

```
ctccctctcc ctccccccc  cccacacatt tgaattcgtg gagttggtaa atgaggggtc   1380
agttctctgt ctgtctgtag ttttgtgtcc acaggatatg actgacattc tcaccacaca   1440
catacaaagt caaaaatagc tgtggccata taaagaatat ggggagagaa aattattcaa   1500
aatctgcaga aaataatgcc aggcctttaa tcctggcacc caggaggcag aagggagaca   1560
gagttctgag tttatgctga gttccaggag tggaagaaag ggccattgcc tttctggtga   1620
ggactgtctt tttaaatcct cccttctgtc cagtactggt aactctgccc aaagcgtgtt   1680
cttcttcctg cctcacaaga ttgcaaagac gttttaacg  aacaatttaa accggtgcaa   1740
cgtttatgcg cagcacacca actcatttaa acaaacaaca gccccataaa atagaaatac   1800
tttataagca gattgccctc cgatgacttc accccgtcac tttttatag  ttgtgtacag   1860 aatcctagca ctgatacagc aacatcagaa atgtttctgc aaatccttcg caaagattcg   1920
gatttcatac tgggcgtggt accctccaaa atgagttgtt tgagctaggg ttgttgggat   1980
ctcagcttgg cgaagttgta gctctttctt ctgaataaaa gatgacacaa ttttctgcta   2040
agatgttaaa taccttaagt ttcagtgtag tgatgaaaat taccctcctt cgttttcta   2100 atacctgggt gttgcactgg ggaggaagga gagatttcga aaggactag  ttcactttct   2160 cagaagacac gtgtgcactt ctttgctgtg cgggtccaga aggagcccag cgtgtcaaag   2220
ggtgaccagg catggggag  gggtgttagc gtgggtagca ggcgggggct gtccgatcct   2280
ttagcgctgt ttcaacgccc agctctcctc ctgaaccctg catctcttct gtagtccggg   2340
ctccatccct ttcccctccc ccatccggag gtgggggaa  cagcagtgtt ttcaggggtg   2400
ttcaattcat gctatattca gggcaaatag cgccacctat ggcgggctgt ggagccaggt   2460
caggagcaga gtgtggctcc cccccccc   cacaccatcc tcagaggaag aaggaggga   2520 cccactggtc acacgactgg gcgattgggc gggcactgaa tctccgcgag gaaagcgaac   2580
tcgaggagag ccatcacgcg tagc                                         2604
```

<210> SEQ ID NO 10
<211> LENGTH: 702
<212> TYPE: DNA
<213> ORGANISM: Artificial Sequence
<220> FEATURE:
<223> OTHER INFORMATION: vector sequence

<400> SEQUENCE: 10

```
atggggagta gcaagagcaa gcctaaggac cccagccagc gctctagagg cgtccaagtc     60
gaaaccatta gtcccggcga tgcagaaca  tttcctaaaa ggggacaaac atgtgtcgtc    120
cattatacag gcatgttgga ggacggcaaa aaggtggaca gtagtagaga tcgcaataaa    180
cctttcaaat tcatgttggg aaaacaagaa gtcattaggg gatgggagga gggcgtggct    240
caaatgtccg tcggccaacg cgctaagctc accatcagcc ccgactacgc atacggcgct    300
accggacatc ccggaattat tcccctcac  gctaccttgg tgtttgacgt cgaactgttg    360
aagctcgaga ctagaggagt gcaggtggag actatctccc caggagacgg cgcaccttc    420 cccaagcgcg gccagacctg cgtggtgcac tacaccggga tgcttgaaga tggaaagaaa    480
gttgattcct cccgggacag aaacaagccc tttaagttta tgctaggcaa gcaggaggtg    540
atccgaggct gggaagaagg ggttgcccag atgagtgtgg gtcagagagc caaactgact    600
atatctccag attatgccta tggtgccact gggcacccag gcatcatccc accacatgcc    660
actctcgtct tcgatgtgga gcttctaaaa ctggaaacta gt                       702
```

```
<210> SEQ ID NO 11
<211> LENGTH: 789
<212> TYPE: DNA
<213> ORGANISM: Homo sapiens

<400> SEQUENCE: 11
agtgaatcac agactttgga caaagtttac caaatgaaaa gcaaacctcg gggatactgt      60
ctgatcatca acaatcacaa ttttgcaaaa gcacgggaga agtgcccaa acttcacagc      120 attagggaca ggaatggaac acacttggat gcagggcgtt tgaccacgac ctttgaagag      180
cttcattttg agatcaagcc ccacgatgac tgcacagtag agcaaatcta tgagattttg      240
aaaatctacc aactcatgga ccacagtaac atggactgct tcatctgctg tatcctctcc      300
catggagaca agggcatcat ctatggcact gatggacagg aggcccccat ctatgagctg      360
acatctcagt tcactggttt gaagtgccct tcccttgctg gaaaacccaa agtgtttttt      420
attcaggctt gtcaggggga taactaccag aaaggtatac ctgttgagac tgattcagag      480
gagcaaccct atttagaaat ggatttatca tcacctcaaa cgagatatat cccggatgag      540
gctgactttc tgctggggat ggccactgtg aataactgtg tttcctaccg aaaccctgca      600
gagggaacct ggtacatcca gtcactttgc cagagcctga gagagcgatg tcctcgaggc      660
gatgatattc tcaccatcct gactgaagtg aactatgaag taagcaacaa ggatgacaag      720
aaaaacatgg ggaaacagat gcctcagcct actttcacac taagaaaaaa acttgtcttc      780
ccttctgat                                                             789

<210> SEQ ID NO 12
<211> LENGTH: 27
<212> TYPE: DNA
<213> ORGANISM: Artificial Sequence
<220> FEATURE:
<223> OTHER INFORMATION: epitope sequence

<400> SEQUENCE: 12
gattacaagg atgacgacga taagtga                                         27

<210> SEQ ID NO 13
<211> LENGTH: 5
<212> TYPE: DNA
<213> ORGANISM: Artificial Sequence
<220> FEATURE:
<223> OTHER INFORMATION: 3'UTR

<400> SEQUENCE: 13 ggatc                                                                 5

<210> SEQ ID NO 14
<211> LENGTH: 39
<212> TYPE: DNA
<213> ORGANISM: Artificial Sequence
<220> FEATURE:
<223> OTHER INFORMATION: multiple cloning site

<400> SEQUENCE: 14
aacctcgagg aattcacgcg tttaattaac tcgaggttt                            39

<210> SEQ ID NO 15
<211> LENGTH: 1268
<212> TYPE: DNA
<213> ORGANISM: Artificial Sequence
<220> FEATURE:
<223> OTHER INFORMATION: combination of IRES and GFP sequences
```

<400> SEQUENCE: 15

```
tcgaggtcga cggtatcgat aagcttgata tcgaattccg ccctctccc tccccccc        60
ctaacgttac tggccgaagc cgcttggaat aaggccggtg tgcgtttgtc tatatgttat     120
tttccaccat attgccgtct tttggcaatg tgagggcccg gaaacctggc cctgtcttct     180
tgacgagcat tcctaggggt cttcccctc tcgccaaagg aatgcaaggt ctgttgaatg      240
tcgtgaagga agcagttcct ctggaagctt cttgaagaca acaacgtct gtagcgaccc      300
tttgcaggca gcggaacccc ccacctggcg acaggtgcct ctgcggccaa aagccacgtg     360
tataagatac acctgcaaag gcggcacaac cccagtgcca cgttgtgagt tggatagttg     420
tggaaagagt caaatggctc tcctcaagcg tattcaacaa ggggctgaag gatgcccaga    480
aggtacccca ttgtatggga tctgatctgg ggcctcggtg cacatgcttt acatgtgttt     540
agtcgaggtt aaaaaaacgt ctaggccccc cgaaccacgg ggacgtggtt ttcctttgaa    600
aaacacgatg ataatatggc cacaaccatg gtgagcaagg gcgaggagct gttcaccggg    660
gtggtgccca tcctggtcga gctggacggc gacgtaaacg gccacaagtt cagcgtgtcc    720
ggcgagggcg agggcgatgc cacctacggc aagctgaccc tgaagttcat ctgcaccacc    780
ggcaagctgc ccgtgccctg gcccaccctc gtgaccaccc tgacctacgg cgtgcagtgc    840
ttcagccgct accccgacca catgaagcag cacgacttct tcaagtccgc catgcccgaa    900
ggctacgtcc aggagcgcac catcttcttc aaggacgacg gcaactacaa gacccgcgcc    960
gaggtgaagt tcgagggcga caccctggtg aaccgcatcg agctgaaggg catcgacttc   1020
aaggaggacg gcaacatcct ggggcacaag ctggagtaca actacaacag ccacaacgtc   1080
tatatcatgg ccgacaagca gaagaacggc atcaaggtga acttcaagat ccgccacaac   1140
atcgaggacg gcagcgtgca gctcgccgac cactaccagc agaacacccc catcggcgac   1200
ggccccgtgc tgctgcccga caaccactac ctgagcaccc agtccgccct gagcaaagac   1260
cccaacga                                                             1268
```

<210> SEQ ID NO 16
<211> LENGTH: 565
<212> TYPE: DNA
<213> ORGANISM: Oryctolagus cuniculus

<400> SEQUENCE: 16

```
gaagcgcgat cacatggtcc tgctggagtt cgtgaccgcc gccgggatca ctctcggcat     60
ggacgagctg tacaagtaaa gcggccgcga tcttttttccc tctgccaaaa attatgggga   120
catcatgaag cccccttgagc atctgacttc tggctaataa aggaaattta ttttcattgc   180
aatagtgtgt tggaattttt tgtgtctctc actcggaagg acatatggga gggcaaatca   240
tttaaaacat cagaatgagt atttggttta gagtttggca acatatgcca tatgctggct   300
gccatgaaca aggtggcta taaagaggtc atcagtatat gaaacagccc cctgctgtcc    360
attccttatt ccatagaaaa gccttgactt gaggttagat ttttttttata ttttgttttg   420
tgttattttt ttcttttaaca tccctaaaat tttccttaca tgttttacta gccagatttt    480
tcctcctctc ctgactactc ccagtcatag ctgtccctct tctcttatga agatccctcg    540
acctgcagcc caagcttggc gtaat                                          565
```

<210> SEQ ID NO 17
<211> LENGTH: 26
<212> TYPE: DNA
<213> ORGANISM: Artificial Sequence
<220> FEATURE:
<223> OTHER INFORMATION: M13 phage

<400> SEQUENCE: 17
catggtcata gctgtttcct gtgtga                                                26

<210> SEQ ID NO 18
<211> LENGTH: 285
<212> TYPE: DNA
<213> ORGANISM: Artificial Sequence
<220> FEATURE:
<223> OTHER INFORMATION: expression vector

<400> SEQUENCE: 18
aattgttatc cgctcacaat tccacacaac atacgagccg aagcataaa gtgtaaagcc     60 tggggtgcct aatgagtgag ctaactcaca ttaattgcgt tgcgctcact gcccgctttc    120
cagtcgggaa acctgtcgtg ccagcggatc cgcatctcaa ttagtcagca accatagtcc   180
cgcccctaac tccgcccatc ccgccccta a ctccgcccag ttccgcccat tctccgcccc  240
atggctgact aattttttt atttatgcag aggccgaggc cgcct                     285

<210> SEQ ID NO 19
<211> LENGTH: 58
<212> TYPE: DNA
<213> ORGANISM: Artificial Sequence
<220> FEATURE:
<223> OTHER INFORMATION: linker sequence

<400> SEQUENCE: 19
aaacggccgg ccatcgatac cgtcgacctc gagggggggc ccggtaccca gcttttgt      58

<210> SEQ ID NO 20
<211> LENGTH: 37
<212> TYPE: DNA
<213> ORGANISM: Artificial Sequence
<220> FEATURE:
<223> OTHER INFORMATION: T3 phage

<400> SEQUENCE: 20 tcccttagt gagggttaat tgcgcgcttg gcgtaat                              37

<210> SEQ ID NO 21
<211> LENGTH: 26
<212> TYPE: DNA
<213> ORGANISM: M13 phage

<400> SEQUENCE: 21
catggtcata gctgtttcct gtgtga                                         26

<210> SEQ ID NO 22
<211> LENGTH: 362
<212> TYPE: DNA
<213> ORGANISM: Artificial Sequence
<220> FEATURE:
<223> OTHER INFORMATION: vector sequence

<400> SEQUENCE: 22
aattgttatc cgctcacaat tccacacaac atacgagccg aagcataaa gtgtaaagcc     60 tggggtgcct aatgagtgag ctaactcaca ttaattgcgt tgcgctcact gcccgctttc    120
cagtcgggaa acctgtcgtg ccagctgcat taatgaatcg gccaacgcgc ggggagaggc   180
ggtttgcgta ttgggcgctc ttccgcttcc tcgctcactg actcgctgcg ctcggtcgtt   240

| cggctgcggc gagcggtatc agctcactca aaggcggtaa tacggttatc cacagaatca | 300 |
| gggataacg caggaaagaa catgtgagca aaaggccagc aaaaggccag gaaccgtaaa | 360 |
| aa | 362 |

<210> SEQ ID NO 23
<211> LENGTH: 780
<212> TYPE: DNA
<213> ORGANISM: Artificial Sequence
<220> FEATURE:
<223> OTHER INFORMATION: ColE1 origin

<400> SEQUENCE: 23

| ggccgcgttg ctggcgtttt tccataggct ccgcccccct gacgagcatc acaaaaatcg |  60 |
| acgctcaagt cagaggtggc gaaacccgac aggactataa agataccagg cgtttccccc | 120 |
| tggaagctcc ctcgtgcgct ctcctgttcc gaccctgccg cttaccggat acctgtccgc | 180 |
| ctttctccct tcgggaagcg tggcgctttc tcatagctca cgctgtaggt atctcagttc | 240 |
| ggtgtaggtc gttcgctcca agctgggctg tgtgcacgaa ccccccgttc agcccgaccg | 300 |
| ctgcgcctta tccggtaact atcgtcttga gtccaacccg gtaagacacg acttatcgcc | 360 |
| actggcagca gccactggta acaggattag cagagcgagg tatgtaggcg gtgctacaga | 420 |
| gttcttgaag tggtggccta actacggcta cactagaagg acagtatttg gtatctgcgc | 480 |
| tctgctgaag ccagttacct tcggaaaaag agttggtagc tcttgatccg gcaaacaaac | 540 |
| caccgctggt agcggtggtt ttttgtttg caagcagcag attacgcgca gaaaaaaagg | 600 |
| atctcaagaa gatcctttga tcttttctac ggggtctgac gctcagtgga acgaaaactc | 660 |
| acgttaaggg attttggtca tgagattatc aaaaaggatc ttcacctaga tccttttaaa | 720 |
| ttaaaaatga agttttaaat caatctaaag tatatatgag taaacttggt ctgacagtta | 780 |

<210> SEQ ID NO 24
<211> LENGTH: 986
<212> TYPE: DNA
<213> ORGANISM: Artificial Sequence
<220> FEATURE:
<223> OTHER INFORMATION: vector sequence

<400> SEQUENCE: 24

| ccaatgctta atcagtgagg cacctatctc agcgatctgt ctatttcgtt catccatagt |  60 |
| tgcctgactc cccgtcgtgt agataactac gatacgggag ggcttaccat ctggccccag | 120 |
| tgctgcaatg ataccgcgag acccacgctc accggctcca gatttatcag caataaacca | 180 |
| gccagccgga agggccgagc gcagaagtgg tcctgcaact ttatccgcct ccatccagtc | 240 |
| tattaattgt tgccgggaag ctagagtaag tagttcgcca gttaatagtt tgcgcaacgt | 300 |
| tgttgccatt gctacaggca tcgtggtgtc acgctcgtcg tttggtatgg cttcattcag | 360 |
| ctccggttcc caacgatcaa ggcgagttac atgatccccc atgttgtgca aaaaagcggt | 420 |
| tagctccttc ggtcctccga tcgttgtcag aagtaagttg gccgcagtgt tatcactcat | 480 |
| ggttatggca gcactgcata attctcttac tgtcatgcca tccgtaagat gcttttctgt | 540 |
| gactggtgag tactcaacca agtcattctg agaatagtgt atgcggcgac cgagttgctc | 600 |
| ttgcccggcg tcaatacggg ataataccgc gccacatagc agaactttaa aagtgctcat | 660 |
| cattggaaaa cgttcttcgg ggcgaaaact ctcaaggatc ttaccgctgt tgagatccag | 720 |
| ttcgatgtaa cccactcgtg cacccaactg atcttcagca tcttttactt tcaccagcgt | 780 |
| ttctgggtga gcaaaaacag gaaggcaaaa tgccgcaaaa aagggaataa gggcgacacg | 840 |

```
gaaatgttga atactcatac tcttcctttt tcaatattat tgaagcattt atcagggtta    900
ttgtctcatg agcggataca tatttgaatg tatttagaaa aataaacaaa tagggttcc    960 gcgcacattt ccccgaaaag tgccac                                        986

<210> SEQ ID NO 25
<211> LENGTH: 24
<212> TYPE: DNA
<213> ORGANISM: Pan troglodytes
<220> FEATURE:
<223> OTHER INFORMATION: caspase 8

<400> SEQUENCE: 25
gaatcacaga ctttggacaa agtt                                          24

<210> SEQ ID NO 26
<211> LENGTH: 22
<212> TYPE: DNA
<213> ORGANISM: Pan troglodytes
<220> FEATURE:
<223> OTHER INFORMATION: caspase 8

<400> SEQUENCE: 26
ggtcaaagcc cctgcatcca ag                                            22

<210> SEQ ID NO 27
<211> LENGTH: 21
<212> TYPE: DNA
<213> ORGANISM: Artificial Sequence
<220> FEATURE:
<223> OTHER INFORMATION: synthetic construct

<400> SEQUENCE: 27
caaactacaa cagccacaac g                                             21

<210> SEQ ID NO 28
<211> LENGTH: 18
<212> TYPE: DNA
<213> ORGANISM: Artificial Sequence
<220> FEATURE:
<223> OTHER INFORMATION: synthetic construct

<400> SEQUENCE: 28
ggtcacgaac tccagcag                                                 18
```

TRANSGENIC ANIMALS CAPABLE OF BEING INDUCED TO DELETE SENESCENT CELLS

CROSS REFERENCE TO RELATED APPLICATIONS

This application is a continuation of U.S. application Ser. No. 14/125,841, filed Mar. 4, 2014, which is a National Stage application under 35 U.S.C. § 371 of International Application No. PCT/US2012043613, having an International Filing Date of Jun. 21, 2012, which claims the benefit of U.S. Provisional Application Ser. No. 61/567,587, filed Dec. 6, 2011 and U.S. Provisional Application Ser. No. 61/499,616, filed Jun. 21, 2011. The disclosures of these prior applications are considered part of (and are incorporated by reference in) the disclosure of this application.

BACKGROUND

1. Technical Field

This document relates to methods and materials involved in the removal of senescent cells within a mammal. For example, this document provides transgenic non-human animals that can be induced to delete senescent cells.

2. Background Information

Cellular senescence, which halts the proliferation of damaged or dysfunctional cells, is widely recognized as an important mechanism to constrain the malignant progression of tumor cells (Campisi, *Curr. Opin. Genet. Dev.*, 21:107-112 (2011); and Kuilman et al., *Genes Develop.*, 24:2463-2479 (2010)). As cells senesce, they can develop a unique phenotype, referred to as the senescence-associated secretory phenotype (SASP, or alternatively called SMS), in which they acquire the ability to secrete a variety of growth factors, cytokines, chemokines, and proteases (Coppe et al., *PLoS Biol.*, 6:2853-2868 (2008)). The observation that senescent cells can accumulate in several tissues and organs during organismal aging and are present at sites of age-related pathologies has led to speculation that they contribute to aging and age-related dysfunction (Campisi, *Cell*, 120:513-522 (2005)).

SUMMARY

This document relates to methods and materials involved in the removal of senescent cells within a mammal. For example, this document provides transgenic non-human animals that can be induced to delete senescent cells (e.g., p16$^{Ink4a}$-positive senescent cells). As described herein, transgenic mice can be produced to contain nucleic acid that allows for the controlled clearance of senescent cells (e.g., p16$^{Ink4a}$-positive senescent cells) by controllably inducing apoptosis of senescent cells while inducing little, or no, apoptosis of non-senescent cells. For example, a transgenic non-human animal provided herein can be allowed to grow and develop for a period of time and then can be treated with a compound (e.g., AP20187) capable of inducing apoptosis of senescent cells within the transgenic animal while inducing little, or no, apoptosis of non-senescent cells within the transgenic animal. As described herein, clearance of senescent cells within a transgenic non-human animal can delay or reduce the likelihood of age-related disorders and can maximize healthy lifespan. In some cases, a transgenic non-human animal provided herein can include nucleic acid encoding a marker polypeptide (e.g., a fluorescent polypeptide such as a green fluorescent protein (GFP)) configured to be expressed by senescent cells with little, or no, expression by non-senescent cells. In some cases, a transgenic non-human animal provided herein can have a genetic background (e.g., a BubR1 hypomorphic (BubR1$^{H/H}$) genetic background) that results in a markedly shortened lifespan with or without exhibiting one or more age-related phenotypes such as infertility, lordokyphosis, sarcopenia, cataracts, fat loss, cardiac arrhythmias, arterial wall stiffening, impaired wound healing, and dermal thinning.

The transgenic non-human animals provided herein can be used in assays designed to identify agents having the ability to kill, or to facilitate the killing of, senescent cells. For example, transgenic non-human animals provided herein can be used as controls (e.g., positive controls) for the successful clearance of senescent cells. In some cases, transgenic non-human animals provided herein can be used as controls (e.g., positive controls) for the successful clearance of senescent cells with minimal or no killing of non-senescent cells.

In some cases, transgenic non-human animals provided herein can be used as test animals in assays designed to identify agents having the ability to kill, or to facilitate the killing of, senescent cells. In such cases, the ability of a test agent to kill, or to facilitate the killing of, senescent cells can be monitored based, at least in part, on the expression of a marker polypeptide (e.g., a fluorescent polypeptide such as GFP) configured to be expressed by senescent cells. In some cases, the ability of the test agent to kill, or to facilitate the killing of, senescent cells can be evaluated by comparing its effects in a particular animal at a first time point to the effects observed in the same animal after treatment with a compound (e.g., AP20187) capable of inducing apoptosis of senescent cells within that transgenic animal at a second time point. Such a comparison can be used to identify test agents that are less effective or at least as effective as the compound capable of inducing apoptosis of senescent cells at the second time point. In some cases, the compound capable of inducing apoptosis of senescent cells can be used at the first time point, and the test agent can be used as the second time point to identify test agents that are more effective than the compound used at the first time point.

In some cases, the transgenic non-human animals provided herein can be used in assays designed to identify agents having the ability to delay or reduce the likelihood of age-related disorders and/or maximize healthy lifespan. For example, transgenic non-human animals provided herein can be used as controls (e.g., positive controls) for the successful delay of age-related disorders and/or for the successful increased duration of a healthy lifespan.

In some cases, transgenic non-human animals provided herein can be used as test animals in assays designed to identify agents having the ability to delay or reduce the likelihood of age-related disorders and/or maximize healthy lifespan. In such cases, the ability of a test agent to delay or reduce the likelihood of age-related disorders and/or maximize healthy lifespan can be monitored based, at least in part, on the expression of a marker polypeptide (e.g., a fluorescent polypeptide such as GFP) configured to be expressed by senescent cells. In some cases, the ability of the test agent to delay or reduce the likelihood of age-related disorders and/or maximize healthy lifespan can be evaluated by comparing its effects in a particular animal at a first time point to the effects observed in the same animal after treatment with a compound (e.g., AP20187) capable of inducing apoptosis of senescent cells within that transgenic animal at a second time point. Such a comparison can be used to identify test agents that are less effective or at least as effective as the compound capable of inducing apoptosis of senescent cells at the second time point. In some cases, the compound capable of inducing apoptosis of senescent cells can be used at the first time point, and the test agent can be used at the second time point to identify test agents that are more effective at delaying or reducing the likelihood of age-related disorders and/or maximizing healthy lifespan than the compound used at the first time point.

In general, one aspect of this document features a transgenic mouse, the nucleated cells of which contain a transgene. The transgene comprises, or consists essentially of, a promoter sequence operably linked to a nucleic acid sequence encoding a polypeptide having the ability to kill a cell or facilitate the killing of a cell when the transgenic mouse is administered a compound, wherein senescent cells of the transgenic mouse express the polypeptide, and wherein the senescent cells of the transgenic mouse are killed when the compound is administered to the transgenic mouse. Less than 10 percent of non-senescent cells of the transgenic mouse can be killed when the compound is administered to the transgenic mouse. The promoter sequence can be a p16$^{Ink4a}$ promoter sequence. The polypeptide can comprise a caspase 8 polypeptide sequence. The polypeptide can comprise a FKBP polypeptide sequence. The polypeptide can be a FKBP-caspase 8 fusion polypeptide. The compound can be AP20187. The genetic background of the transgenic mouse can be a BubR1$^{H/H}$ genetic background. The transgene can comprise nucleic acid encoding a marker polypeptide. The marker polypeptide can be a GFP polypeptide.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

Error bars, s.e.m.; n=6 female mice per genotype; *, P=0.0016 and **, P=0.0015, unpaired t tests.

FIG. 6. Age-associated traits of BubR1 hypomorphic mice that are $p16^{Ink4a}$-independent are not influenced by clearance of $p16^{Ink4a}$-positive cells. A, The percentage of sinus pause rhythm disturbances is similarly increased in both treated and non-treated BubR1$^{H/H}$:INK-ATTAC heart tissue. Abbreviation: BPM, beats per minute. B, Thinning of the aorta is not corrected by drug treatment in BubR1$^{H/H}$:INK-ATTAC animals. Error bars, s.e.m.; n=6 female mice per genotype. Consistent with this, $p16^{Ink4a}$ and the INK-ATTAC transgene are not expressed in this tissue. Error bars, s.d.; n=3. FIG. 6C is a graph plotting overall survival for the indicated mice.

Figure 7:
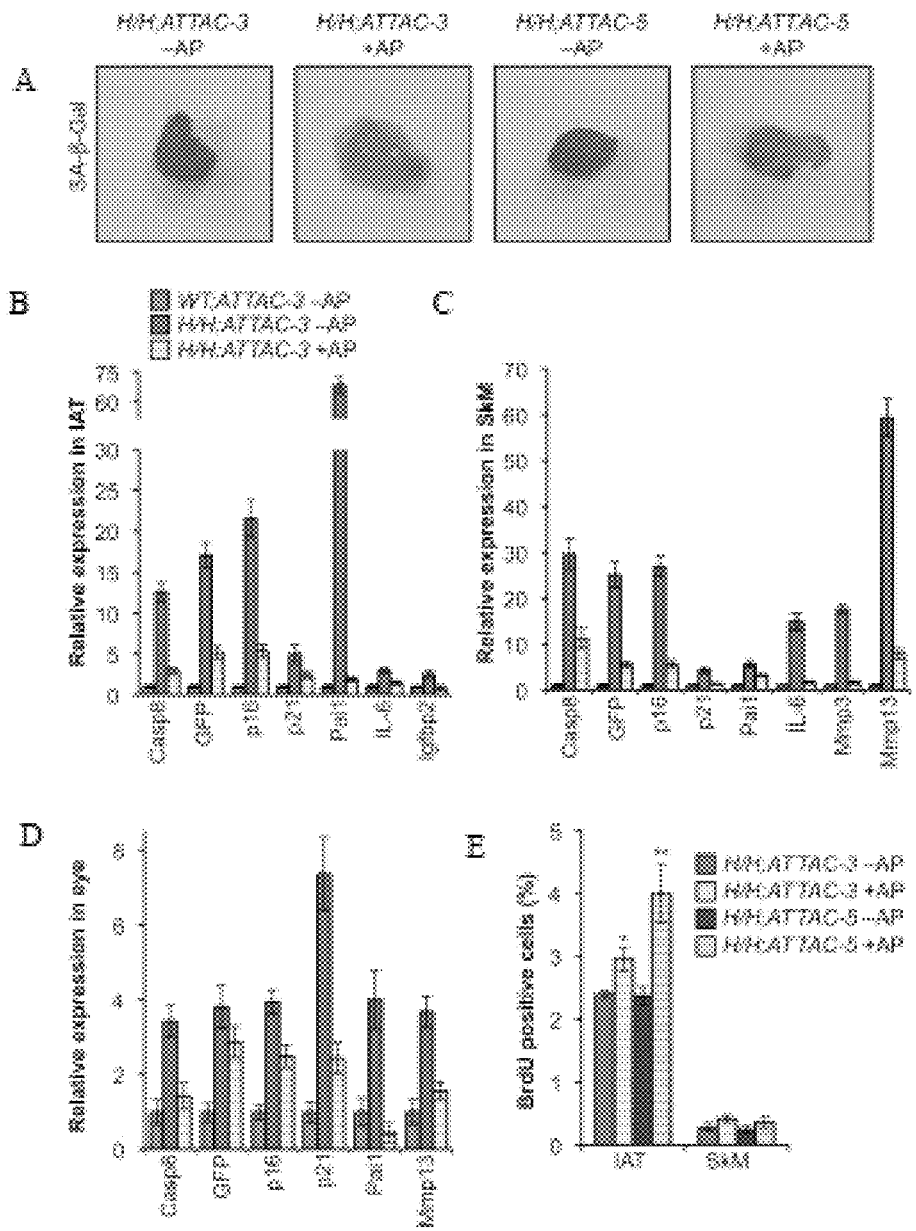

FIG. 7. AP20187-treated BubR1$^{14H}$:INK-ATTAC animals have reduced numbers of $p16^{Ink4a}$-positive senescent cells. A, SA-β-Gal staining of IAT reveals that AP20187-treated adipose tissue attenuates the senescent phenotype driven by BubR1 hypomorphism. qRT-PCR analysis for indicators of senescence in IAT. B-D, Treatment of BubR1$^{H/H}$:INK-ATTAC animals with AP20187 leads to lower levels of senescence-associated markers in IAT (B), skeletal muscle (C), and eye (D). Error bars, s.d.; n=3 female mice per genotype. E, BrdU incorporation rates as a measure of replicative senescence are elevated in IAT and skeletal muscle of BubR1$^{H/H}$:INK-ATTAC mice. Error bars, s.e.m.; n=6 mice per genotype. Statistical analysis was by unpaired t test: *, P=0.0146 and **, P=0.0137.

Figure 8:
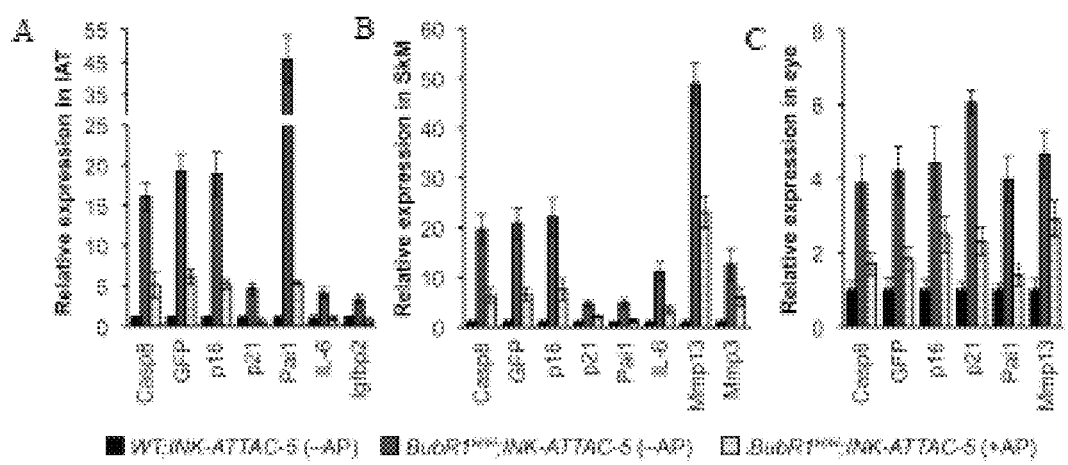

FIG. 8 contains graphs plotting the relative expression of the indicated polypeptides in IAT (A), skeletal muscle (B), and eye (C).

FIG. 9 is a listing of the nucleic acid sequence of a pBLUESCRIPT II KS vector containing a $p16^{Ink4a}$-ATTAC-IRES-GFP nucleic acid construct.

FIG. 10 is a listing of the nucleic acid sequence of FIG. 9 with the various vector components and construct components labeled.

DETAILED DESCRIPTION

This document relates to methods and materials involved in the removal of senescent cells within a mammal. For example, this document provides transgenic non-human animals that can be induced to delete senescent cells (e.g., $p16^{Ink4a}$-positive senescent cells). Such non-human animals can be farm animals such as pigs, goats, sheep, cows, horses, and rabbits, rodents such as rats, guinea pigs, and mice, and non-human primates such as baboons, monkeys, and chimpanzees. The term "transgenic non-human animal" as used herein includes, without limitation, founder transgenic non-human animals as well as progeny of the founders, progeny of the progeny, and so forth, provided that the progeny retain the transgene. The nucleated cells of the transgenic non-human animals provided herein can contain a transgene that includes a promoter sequence (e.g., a $p16^{Ink4a}$ promoter sequence) operably linked to a nucleic acid sequence encoding a polypeptide capable of killing a cell or capable of facilitating the killing of a cell. A promoter sequence of a transgene described herein can be one that drives polypeptide expression in senescent cells while driving less, little, or no expression in non-senescent cells. Examples of such promoters include, without limitation, a $p16^{Ink4a}$ promoter sequence, a $p21^{cip}$ promoter sequence, and a Pai1 promoter sequence.

In some cases, a polypeptide capable of killing a cell or capable of facilitating the killing of a cell can be a polypeptide that includes two polypeptide sequences fused together (e.g., a fusion polypeptide). An example of such a fusion polypeptide can be a FKBP-caspase 8 fusion protein. See, e.g., Pajvani et al., Nat. Med., 11:797-803 (2005). Other examples of polypeptides capable of killing a cell or capable of facilitating the killing of a cell that can be used as described herein include, without limitation, a FKBP-caspase-1 fusion polypeptide or FKBP-caspase-3 fusion polypeptide. In some cases, a polypeptide capable of killing a cell or capable of facilitating the killing of a cell can be engineered to include a tag (e.g., a Flag tag). In some cases, a transgene provided herein can include nucleic acid encoding a marker polypeptide such as a fluorescent polypeptide (e.g., GFP, BFP, or RFP). For example, a transgene provided herein can include nucleic acid encoding a polypeptide capable of killing a cell or capable of facilitating the killing of a cell followed by an internal ribosome entry site followed by a marker polypeptide (e.g., GFP).

In some cases, a transgene can include a $p16^{Ink4a}$ promoter sequence followed by nucleic acid encoding an FKBP-caspase 8 fusion protein. In such cases, administration of a compound such as AP20187 can result in apoptosis of cells expressing the FKBP-caspase 8 fusion protein. For example, senescent cells of a transgenic non-human animal provided herein can express the FKBP-caspase 8 fusion protein of a transgene by virtue of the $p16^{Ink4a}$ promoter sequence and can be selectively and controllably killed following administration of AP20187. AP20187 can be obtained as described elsewhere (U.S. Patent Application Publication No. 2004/0006233).

The term "operably linked" as used herein refers to positioning a regulatory element (e.g., a promoter sequence, an inducible element, or an enhancer sequence) relative to a nucleic acid sequence encoding a polypeptide in such a way as to permit or facilitate expression of the encoded polypeptide. In the transgenes disclosed herein, for example, a promoter sequence (e.g., a $p16^{Ink4a}$ promoter sequence) can be positioned 5' relative to a nucleic acid encoding a polypeptide (e.g., an FKBP-caspase 8 fusion protein).

Various techniques known in the art can be used to introduce transgenes into non-human animals to produce founder lines, in which the transgene is integrated into the genome. Such techniques include, without limitation, pronuclear microinjection (See, e.g., U.S. Pat. No. 4,873,191), retrovirus mediated gene transfer into germ lines (Van der Putten et al., Proc. Natl. Acad. Sci. USA, 82:6148-1652 (1985)), gene targeting into embryonic stem cells (Thompson et al., Cell 56:313-321 (1989)), electroporation of embryos (Lo, Mol. Cell. Biol., 3:1803-1814 (1983)), and in vitro transformation of somatic cells, such as cumulus or mammary cells, followed by nuclear transplantation (Wilmut et al., Nature, 385:810-813 (1997); and Wakayama et al., Nature, 394:369-374 (1998)). For example, fetal fibroblasts can be genetically modified to contain an INK-ATTAC construct (FIG. 1A), and then fused with enucleated oocytes. After activation of the oocytes, the eggs are cultured to the blastocyst stage. See, for example, Cibelli et al., Science, 280:1256-1258 (1998). Standard breeding techniques can be used to create animals that are homozygous for the transgene from the initial heterozygous founder animals. Homozygosity is not required, however, as the phenotype can be observed in hemizygotic animals.

Once transgenic non-human animals have been generated, expression of an encoded polypeptide (e.g., an FKBP-caspase 8 fusion protein or marker polypeptide) can be assessed using standard techniques. Initial screening can be accomplished by Southern blot analysis to determine whether or not integration of the transgene has taken place.

For a description of Southern analysis, see sections 9.37-9.52 of Sambrook et al., 1989, *Molecular Cloning, A Laboratory Manual*, second edition, Cold Spring Harbor Press, Plainview; NY. Polymerase chain reaction (PCR) techniques also can be used in the initial screening. PCR refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. PCR is described in, for example *PCR Primer: A Laboratory Manual*, ed. Dieffenbach and Dveksler, Cold Spring Harbor Laboratory Press, 1995. Nucleic acids also can be amplified by ligase chain reaction, strand displacement amplification, self-sustained sequence replication, or nucleic acid sequence-based amplified. See, for example, Lewis, *Genetic Engineering News*, 12:1 (1992); Guatelli et al., *Proc. Natl. Acad. Sci. USA*, 87:1874-1878 (1990); and Weiss, *Science*, 254:1292-1293 (1991).

Expression of a nucleic acid sequence encoding a polypeptide (e.g., an FKBP-caspase 8 fusion protein or marker polypeptide) in senescent cells of transgenic non-human animals can be assessed using techniques that include, without limitation, Northern blot analysis of tissue samples obtained from the animal, in situ hybridization analysis, Western analysis, immunoassays such as enzyme-linked immunosorbent assays, and reverse-transcriptase PCR (RT-PCR). As described herein, expression of an FKBP-caspase 8 fusion protein by senescent cells within the transgenic animal can result in transgenic animals that can be treated with AP20187 such that the senescent cells are killed. Such transgenic animals can exhibit delayed, or a reduced likelihood of, age-related disorders and/or a maximized healthy lifespan. It is understood that a particular phenotype in a transgenic animal typically is assessed by comparing the phenotype in the transgenic animal to the corresponding phenotype exhibited by a control non-human animal that lacks the transgene.

A transgenic non-human animal provided herein can have any appropriate genetic background. In some cases, a transgenic non-human animal provided herein can have a BubR1 hypomorphic (BubR1$^{H/H}$) genetic background, a Tert$^{-/-}$ genetic background, or a bGF$^+$ (bovine growth hormone) genetic background.

This document also provides tissues (e.g., skin, eye, fat, muscle, lung, heart, bone, liver, intestine, kidney, spleen, brain, cartilage, marrow, adrenal glands, ovaries, and testes) and cells (e.g., fat cells, preadipocytes, skin or lung fibroblasts, muscle satellite cells, osteoblasts, bone marrow progenitor cells, neuronal progenitor cells, hepatocytes, endothelial cells, chondroblasts, and splenocytes cells) obtained from a transgenic non-human animal provided herein.

This document also provides methods for identifying agents having the ability to kill, or to facilitate the killing of, senescent cells and methods for identifying agents having the ability to delay, or reduce the likelihood of age-related disorders, and/or maximize healthy lifespan. Such methods can include, for example, (1) targeting senescent cells based on compounds activated by enzyme activities that are higher in them than other cells (such as senescence-associated (β-galactosidase), such compounds killing the senescent cells upon activation, (2) use of compounds that kill cells to which they bind through receptors that are more highly expressed by senescent than other cells (such receptors being identified by proteomic or expression profiling of senescent versus non-senescent cells or other approaches), or (3) compounds that are activated by metabolic processes that are more active in senescent than non-senescent cells (with such metabolic processes being identified through metabolomic, proteomic, expression profiling, or other means), with the compounds so activated killing the senescent cell.

In some cases, methods for identifying agents having the ability to kill, or to facilitate the killing of, senescent cells and methods for identifying agents having the ability to delay, or reduce the likelihood of age-related disorders, and/or maximize healthy lifespan can include obtaining senescent cells from a mammal (e.g., an animal model or a human). For example, a transgenic mouse provided herein such as a transgenic mouse that expresses a marker polypeptide (e.g., GFP) in senescent cells can be used to obtain senescent cells. Such a transgenic mouse can contain a transgene that includes a marker polypeptide (e.g., GFP) operably linked to a promoter sequence that drives polypeptide expression in senescent cells while driving less, little, or no expression in non-senescent cells. Examples of such promoters include, without limitation, a p16$^{Ink4a}$ promoter sequence, a p21cip promoter sequence, and a Pai1 promoter sequence. The senescent cell can be any appropriate cell type or from any appropriate tissue. For example, senescent cells can be obtained from fat or endothelial tissue. In some cases, senescent cells can be obtained from liver, bone marrow, heart, lung, or skin tissue.

Any appropriate method can be used to obtain senescent cells from a mammal. For example, senescent cells expressing a marker polypeptide (e.g., GFP) under the control of a p16$^{Ink4a}$ promoter sequence can be separated from non-senescent cells using standard techniques such as cell sorting methods based on the expression of the marker polypeptide. In some cases, cell lines of senescent cells can be used in place of freshly obtained senescent cells to identify agents having the ability to kill, or to facilitate the killing of, senescent cells and agents having the ability to delay, or reduce the likelihood of age-related disorders, and/or maximize healthy lifespan as described herein. In some cases, senescent cells can be obtained by cell passage in culture (e.g., greater than about 12 to 15 cell passages for mouse embryonic fibroblasts and greater than about 20 cell passages at a 1:2 split ratio for human cells) or by radiation treatment (e.g., treatment with about 5 to about 50 Grays), a ceramide (e.g., C6, C16, or C18) treatment (e.g., treatment with about 7 µM to about 15 µM (e.g., 13 µM) of ceramide such as C16 for at least about 15 days), exposure to oncogenes or increased expression of oncogenes such as H-Ras or K-Ras (e.g., K-RasG12V), exposure to non-oncogenes or increased expression of non-oncogenes such as JAK or STAT, or exposure to glucose (e.g., about 16.5 mM to about 22.5 mM of D-glucose) for at least 10 days (e.g., greater than 30 days). In some cases, senescent cells can be obtained by exposing cells to reactive oxygen species or hydrogen peroxide to induce senescence via a p53 pathway.

Once obtained, the senescent cells can be exposed to a library of test agents individually or in pools to identify those agents or pools of agents having the ability to kill, or to facilitate the killing of, the senescent cells. Once identified as having the ability to kill, or to facilitate the killing of, the senescent cells, the identified agent can be applied to comparable non-senescent cells in comparable concentrations to confirm that the agent has a reduced ability to kill, or to facilitate the killing of, non-senescent cells. Those agents having the ability to kill, or to facilitate the killing of, senescent cells with a reduced or no ability to kill, or to facilitate the killing of, non-senescent cells can be classified as being an agent having the ability to delay, or reduce the likelihood of age-related disorders, and/or maximize healthy lifespan. In some cases, senescent cells obtained from a transgenic mammal provided herein and treated in a manner that results in senescent cell death can be used as positive controls.

In some cases, an agent can be identified as having the ability to kill, or to facilitate the killing of, senescent cells or as having the ability to delay, or reduce the likelihood of age-related disorders, and/or maximize healthy lifespan using in vivo techniques. For example, an animal model such as wild-type mice or animals, mice with a BubR1 hypomorphic (BubR1$^{H/H}$) genetic background, or other mouse or animal models can be used. In such cases, a library of test agents can be administered individually or in pools to the animals (e.g., mice), and the animals (e.g., mice) can be assessed for indications that the test agent is capable of killing, or facilitating the killing of, senescent cells or is capable of delaying, or reducing the likelihood of age-related disorders, and/or maximizing healthy lifespan. Indications of senescent cell killing or indications of delayed or reduced likelihood of age-related disorders, and/or indications of maximized healthy lifespan can be detected and assessed as described herein. For example, the ability of an agent to increase the length of lifespan can be assessed comparing treated and untreated mice with, for example, a BubR1 hypomorphic (BubR1$^{H/H}$) genetic background.

This document also provides methods and materials for identifying molecules (e.g., polypeptides, carbohydrates, lipids, and nucleic acids) possessed or expressed by senescent cells. For example, senescent cells can be obtained as described herein and assessed to identify molecules (e.g., polypeptides) possessed or expressed by those senescent cells. Any appropriate method can be used to identify molecules possessed or expressed by senescent cells. For example, polypeptide isolation and sequencing techniques can be used to identify polypeptides expressed by senescent cells.

In some cases, a transgenic mouse provided herein can be used to identify molecules (e.g., polypeptides and carbohydrates) possessed or expressed by senescent cells. For example, a transgenic mouse provided herein can be treated with a compound (e.g., AP20187) starting at or before birth (e.g., shortly after fertilization via treatment of the mouse's mother) such that senescent cells are killed or prevented from developing. In such cases, the resulting mouse can be immunologically naïve with respect to the molecules exclusively expressed by senescent cells. The immunologically naïve mouse can then be exposed to senescent cells or components from senescent cells (e.g., plasma membranes) in a manner designed to trigger an immune response. Resulting antibodies or antibody-producing cells can be isolated and assessed to confirm that the antibodies recognize a molecule presented or expressed by senescent cells. In some cases, the antibodies can be assessed for the ability to not recognize molecules presented or expressed by non-senescent cells. Once such antibodies are obtained, they can be used to identify the molecule present or expressed by the senescent cells.

In some cases, antibodies directed to a molecule present or expressed by senescent cells can be used to kill, or to facilitate the killing of, senescent cells or to delay, or reduce the likelihood of age-related disorders, and/or to maximize healthy lifespan. For example, antibodies directed to a molecule present or expressed by senescent cells can be conjugated with isotopes or toxins to form conjugates having the ability to kill, or to facilitate the killing of, senescent cells or as having the ability to delay, or reduce the likelihood of age-related disorders, and/or maximize healthy lifespan.

The invention will be further described in the following examples, which do not limit the scope of the invention described in the claims.

EXAMPLES

Example 1

Figure 1:
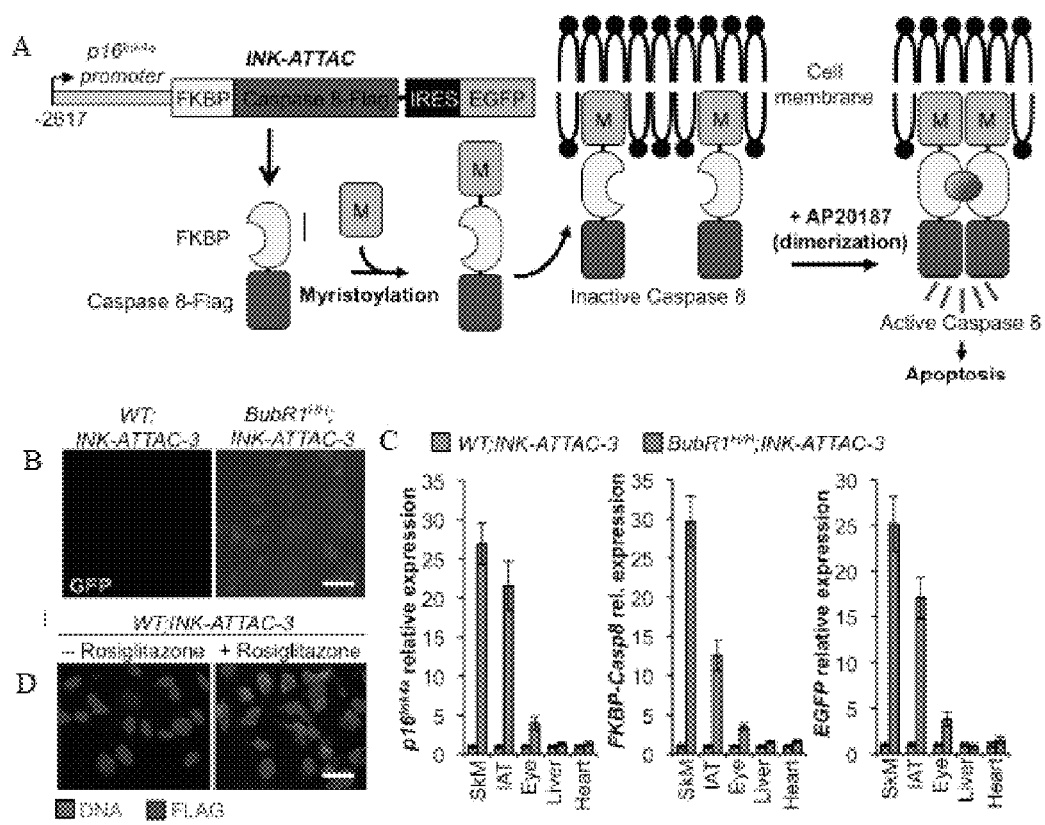
FIG. 1. p16$^{Ink4a}$-specific expression of the INK-ATTAC transgene. A, Schematic representation of the INK-ATTAC transgenic construct and the mechanism of apoptosis activation. B, GFP intensity of TAT collected from 5-month-old untreated mice with the indicated genotypes. C, qRT-PCR analysis of untreated 9-month-old mouse tissue analyzed for relative expression of p16$^{Ink4a}$ (left), FKBP-Casp8 (middle), and EGFP (right). Error bars, s.d.; n=3 female mice per genotype. Abbreviation: SkM, skeletal muscle (gastrocnemius). D, Cultured bone marrow cells from 2-month-old WT:INKATTAC-3 mice treated with rosiglitazone for 48 hours and immunostained for Flag antibody (visualizing Flag-FKBP-Casp8). Scale bar, 20 µm.

Clearance of p16$^{Ink4a}$-Positive Senescent Cells Delays Aging-Associated Disorders To examine the role of senescence in aging and age-related pathologies and to test whether elimination of senescent cells has beneficial effects, a transgenic strategy that enabled clearance of senescent cells in mice was designed. A 2617-bp fragment of the p16$^{Ink4a}$ gene promoter, which is transcriptionally active in senescent, but not non-senescent, cells (Wang et al., *J. Biol. Chem.*, 276:48655-48661 (2001)), was engineered into a nucleic acid construct upstream of nucleic acid encoding a FKBP-caspase 8 fusion protein containing a Flag tag (Pajvani et al., *Nat. Med.*, 11:797-803 (2005)) to create an INK-ATTAC construct (FIG. 1A). As shown in FIG. 1A, the INK-ATTAC construct was designed to express the FKBP-caspase 8 fusion protein within senescent cells. Once myristoylated, the FKBP-caspase 8 fusion protein becomes membrane-bound, and addition of AP20187, a synthetic drug, is capable of inducing dimerization of the membrane-bound myristoylated FKBP-caspase 8 fusion protein, thereby inducing apoptosis.

In addition, an internal ribosome entry site (IRES) followed by an open reading frame coding for EGFP was added downstream of the nucleic acid encoding the FKBP-caspase 8 fusion protein (FIG. 1A). The nucleic acid encoding EGFP was added to allow for detection and collection of p16$^{Ink4a}$-positive senescent cells. Injection of the resulting construct into fertilized eggs yielded nine transgenic INK-ATTAC founder lines.

To examine whether removal of p16$^{Ink4a}$-expressing cells is technically feasible and whether this impacts age-associated deficits in mice, each of the founder lines were bred onto a BubR1 hypomorphic (BubR1$^{H/H}$) genetic background. BubR1$^{H/H}$ mice have a markedly shortened lifespan and exhibit a variety of age-related phenotypes including, without limitation, infertility, lordokyphosis, sarcopenia, cataracts, fat loss, cardiac arrhythmias, arterial wall stiffening, impaired wound healing, and dermal thinning (Baker et al., *Nat. Genet.*, 36:744-749 (2004); Hartman et al., *Neurobiol. Aging*, 28:921-927 (2007); and Matsumoto et al., *Stroke*, 38:1050-1056 (2007)). BubR1$^{H/H}$ mice can accumulate p16$^{Ink4a}$-positive cells in several tissues in which age-associated pathologies develop including, without limitation, adipose tissue, skeletal muscle, and eye.

Figure 2:
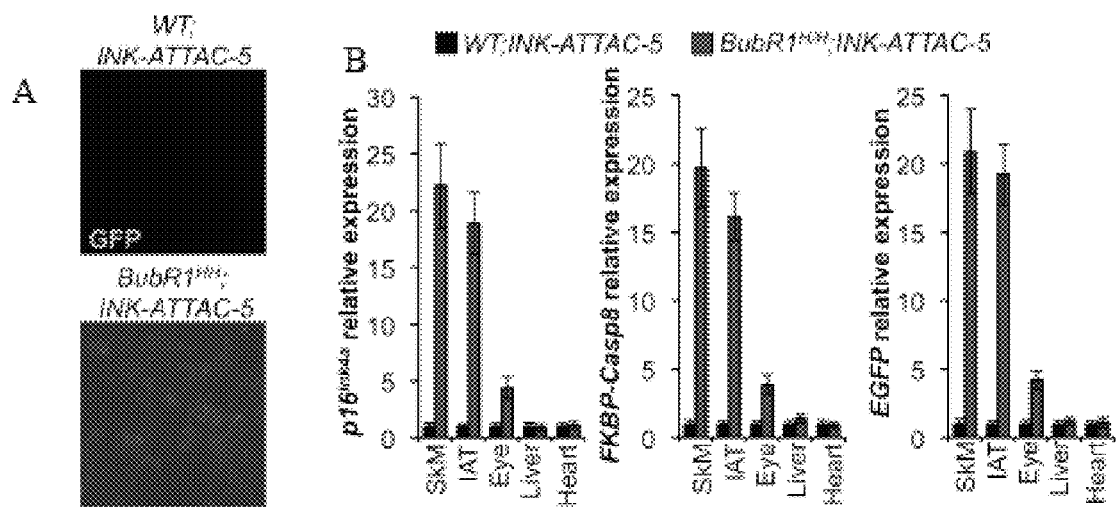
FIG. 2. Validation of p16$^{Ink4a}$-specific expression of the INK-ATTAC-5 transgene. A, GFP intensity of TAT collected from 5-month-old untreated mice with the indicated genotypes. Scale bar, 20 µm. B, qRT-PCR analysis of untreated 9-month-old mouse tissue analyzed for the relative expression of p16$^{Ink4a}$ (left), FKBP-Casp8 (middle), and EGFP (right). Error bars, s.d.; n=3 female mice per genotype. Abbreviation: SkM, skeletal muscle (gastrocnemius).

To screen for transgene activity in p16$^{Ink4a}$-positive cells, samples of inguinal adipose tissue (IAT) were collected from each of the nine BubR1$^{H/H}$:INK-ATTAC strains at five months of age and analyzed for GFP expression by fluorescence microscopy. GFP fluorescence was observed in two of these strains, BubR1$^{H/H}$:INK-ATTAC-3 and BubR1$^{H/H}$:INK-ATTAC-5 (FIGS. 1B and 2A). Next, the extent to which expression of INK-ATTAC and endogenous p16$^{Ink4a}$ overlap was determined using a quantitative (q)RT-PCR approach. Consistent with earlier data from BubR1$^{H/H}$ mice (Baker et al., *Nat. Cell Biol.*, 10:825-836 (2008)), skeletal muscle, IAT, and eye exhibited increased p16$^{Ink4a}$ expression with aging (FIGS. 1C and 2B). BubR1$^{H/H}$:INK-ATTAC-3 and BubR1$^{H/H}$:INK-ATTAC-5 mice also exhibited elevated INK-ATTAC and GFP transcript levels in these tissues. On the other hand, BubR1$^{H/H}$ tissues in which p16$^{Ink4a}$ is not induced, such as brain, lung, colon, liver, and heart, had no clear induction of INK-ATTAC or GFP in BubR1$^{H/H}$:INK-ATTAC-3 and BubR1$^{H/H}$:INK-ATTAC-5 mice (FIGS. 1C and 2B).

To confirm that transgenic INK-ATTAC and endogenous p16$^{Ink4a}$ are under the same transcriptional control mechanism outside the context of BubR1 hypomorphism, bone marrow of wildtype (WT):INK-ATTAC transgenic lines 3 and 5 were harvested and cultured in the absence or presence of rosiglitazone, a drug that can induce cellular senescence and p16$^{Ink4a}$ expression through activation of PPARγ (Gan et al., *J. Cell Sci.* 121:2235-2245 (2008)) Immunofluorescence microscopy revealed that a high proportion of cells expressed Flag-tagged FKBP-Casp8 fusion protein in the presence of rosiglitazone, but not in its absence (FIG. 1D). Together, these data indicated that INK-ATTAC gene activity in the two transgenic founder lines overlaps with endogenous p16$^{Ink4a}$ expression.

Figure 3:
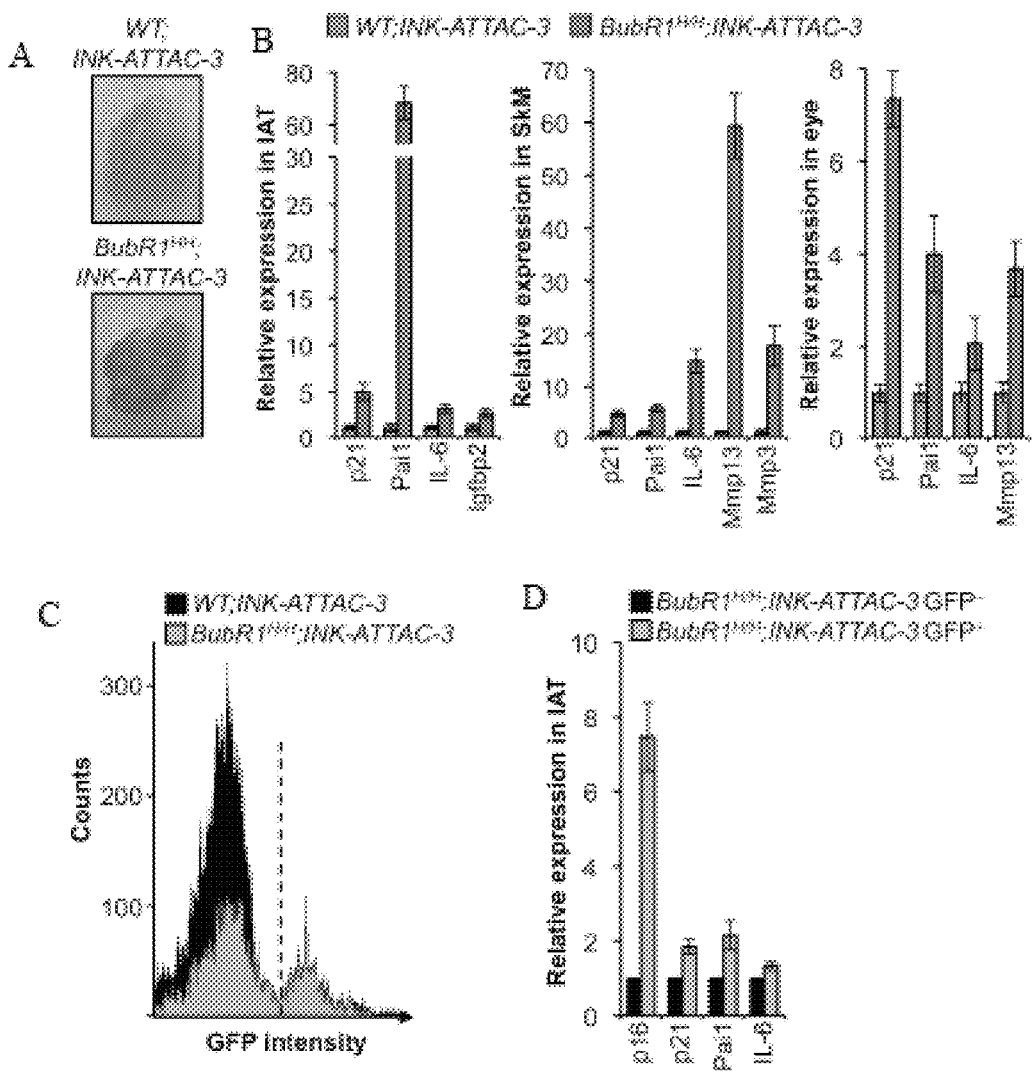
FIG. 3. Tissues expressing the INK-ATTAC transgene have high levels of cellular senescence markers. A, SA-β-Gal staining of TAT in 9-month-old untreated mice with the indicated genotypes. B, qRT-PCR analysis of the indicated tissues for selected markers of senescence. Tissues were collected from 9-month-old untreated mice with the indicated genotypes. Abbreviation: SkM, skeletal muscle (gastrocnemius). C, Representative FACS profile of single-cell suspensions of TAT reveals two distinct cell populations based on GFP intensity of untreated BubR1$^{H/H}$:INK-ATTAC-3 mice (dashed line indicates GFP$^-$ versus GFP$^+$ cells). D, Sorted GFP$^+$ cells from TAT express higher levels of senescence-associated genes than GFP$^-$ cells. For B and D: error bars, s.d.; n=3 female mice per genotype.
Figure 4:
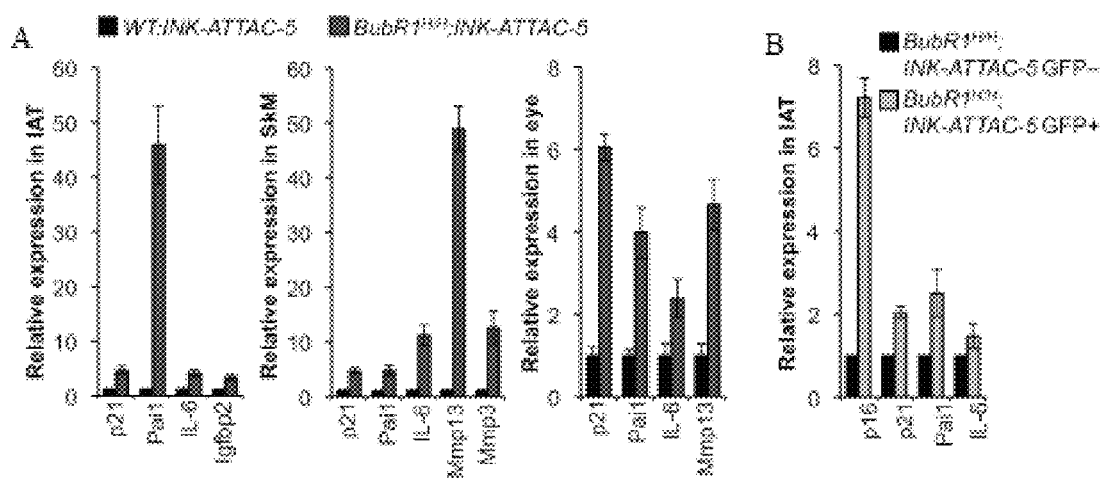
FIG. 4. Tissues expressing the INK-ATTAC-5 transgene display elevated indicators of senescence. A, qRT-PCR analysis of the indicated tissues for selected markers of senescence. Tissues were collected from 9-month-old untreated mice with the indicated genotypes. Abbreviation: SkM, skeletal muscle (gastrocnemius). B, Sorted GFP$^+$ cells from IAT express higher levels of senescence-associated genes than GFP$^-$ cells. For A and B, error bars, s.d.; n=3 female mice per genotype.

Next, the following was performed to determine whether INK-ATTAC is expressed in senescent cells in BubR1 hypomorphic tissue. Fat tissue of aged BubR1$^{H/H}$:INK-ATTAC mice was strongly positive for senescence-associated-β-galactosidase (SA-β-Gal; FIG. 3A). qRT-PCR analysis demonstrated that INK-ATTAC expression correlates with expression of senescence markers in IAT, including p21, Pai1, IL-6, and Igfbp2 (FIGS. 3B and 4A). Skeletal muscle and lens tissue of aged BubR1$^{H/H}$:INK-ATTAC mice were SA-β-Gal negative, but both these tissues expressed other markers of senescence, including Mmp13, Pai1, p21, and IL6 (FIGS. 3B and 4A). To obtain additional evidence for selective expression of INK-ATTAC in senescent cells, IAT was collected from aged BubR1$^{H/H}$:INK-ATTAC animals. Single-cell suspensions were prepared by collagenase treatment, and GFP$^+$ and GFP$^-$ cell populations were separated by fluorescence activated cell sorting (FACS; FIG. 3C). Each population was analyzed for expression of INK-ATTAC and senescence markers by qRT-PCR. GFP$^+$ cells not only expressed much higher levels of p16$^{Ink4a}$ than GFP$^-$ cells, but also exhibited elevated levels of other key senescence markers for IAT (FIGS. 3D and 4B).

Senescence markers in GFP$^-$ cells from BubR1$^{H/H}$:INK-ATTAC mice were as low as in GFP$^-$ cells from age-matched WT:INK-ATTAC mice. Taken together, these results indicated that INK-ATTAC is selectively expressed in p16$^{Ink4a}$-positive senescent cells.

Figure 5:
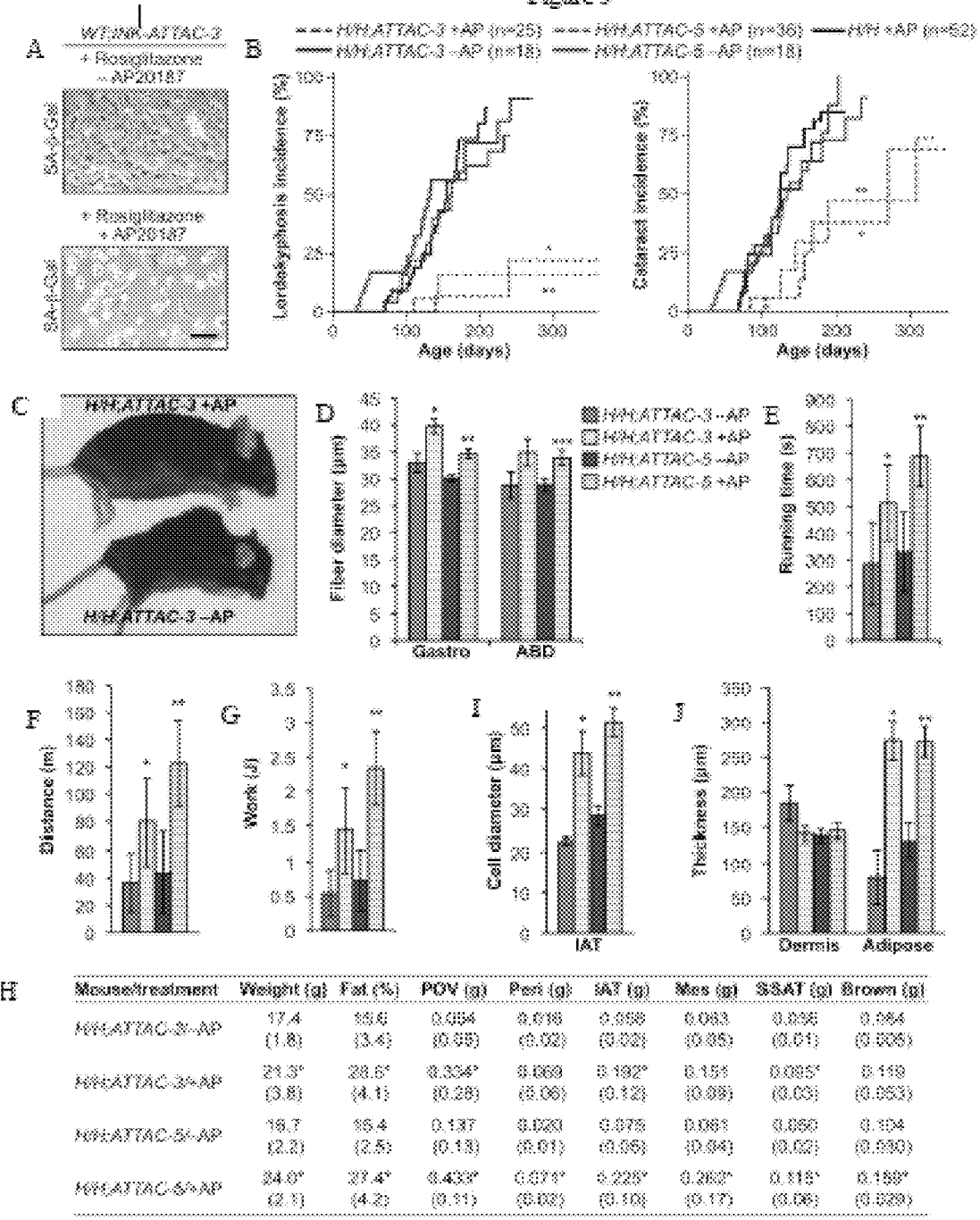
FIG. 5. Delayed onset of p16$^{Ink4a}$-mediated age-related phenotypes in AP20187-treated BubR1$^{H/H}$:INK-ATTAC mice. A, Bone marrow cells collected from 2-month-old WT:INK-ATTAC-3 mice were exposed to rosiglitazone for 5 days to induce senescence and then cultured in the presence or absence of AP20187. After 48 hours, cells were stained for SA-β-Gal. Scale bar, 50 µm. B, Lordokyphosis (left) and cataracts (right) are significantly delayed when BubR1$^{H/H}$:INK-ATTAC transgenic mice were continuously treated with AP20187 from weaning age on. Lordokyphosis: *, P<0.0001 and **, P=0.0077; cataracts: *, P=0.0017 and **, P=0.0158 log-rank tests. C, Representative images of 9-month-old AP20187 treated (top) and untreated (bottom) BubR1$^{H/H}$: INKATTAC-3 mice. D, AP20187 treatment increases average muscle fiber diameter of gastrocnemius (Gastro) and abdominal (ABD) muscles of BubR1$^{H/H}$:INK-ATTAC mice. Error bars, s.e.m.; n=6 mice per genotype. *, P=0.0157; , P=0.0007; *, P=0.0239, unpaired t tests. E, Duration of exercise to exhaustion reveals that AP20187-treated BubR1$^{H/H}$:INK-ATTAC mice have extended running time. Error bars, s.d.; n=6 mice per genotype; *, P=0.0236; **, P=0.0009, unpaired t tests. F, BubR1$^{H/H}$:INK-ATTAC mice treated with AP20187 travel longer distances on a treadmill. Error bars, s.d.; n=6 mice per genotype; *, P=0.0187; **, P=0.0012, unpaired t tests. G, AP20187-treated BubR1$^{H/H}$:INK-ATTAC mice exert more energy during exercise ability tests. Error bars, s.d.; n=6 mice per genotype; *, P=0.0065; **, P=0.0002, unpaired t tests. H, Sizes of various fat depots of BubR1$^{H/H}$:INK-ATTAC transgenic mice are increased in response to AP20187 treatment. Parentheses, s.d.; n=6 mice per genotype. Asterisks denote significant (P<0.05) changes compared to untreated animals of the same transgenic line, unpaired t tests. Abbreviations: POV, paraovarian; Peri, perirenal; Mes, mesenteric; SSAT, subscapular adipose tissue. Total fat percentage was determined by DEXA scanning I, Cell diameter of IAT in BubR1$^{H/H}$:INK-ATTAC mice increases in response to AP20187 treatment. Error bars, s.e.m.; n=6 female mice per genotype; *, P=0.0031; **, P=0.0003, unpaired t tests. J, Dermal and subcutaneous adipose layer thickness of BubR1$^{H/H}$:INK-ATTAC mice indicates consistently increased adiposity with treatment.

To determine whether INK-ATTAC can eliminate senescent cells, bone marrow cells of WT:INK-ATTAC transgenic lines 3 and 5 were cultured in the presence of rosiglitazone to induce senescence, and cell survival was monitored after activating the FKBP-Casp8 fusion protein by AP20187 treatment. The vast majority of cells from both transgenic lines were found to be either dead or in the process of dying 48 hours after adding AP20187 (FIG. 5A). In contrast, parallel cultures that remained untreated consisted almost entirely of viable SA-β-Gal-positive cells. These data demonstrated that FKBP-Casp8 activation efficiently eliminates p16$^{Ink4a}$-positive senescent cells in vitro.

The following was performed to examine whether clearance of p16$^{Ink4a}$-expressing cells from BubR1$^{H/H}$ mice prevents or delays the onset of age-related phenotypes in this progeroid background. To this end, cohorts of BubR1$^{H/H}$:INK-ATTAC-3 and BubR1$^{H/H}$:INK-ATTAC-5 mice were established, which were either treated with AP20187 every third day beginning at 3 weeks of age or left untreated. Both treated and untreated mice were monitored for development of age-associated deficits known to accompany p16$^{Ink4a}$ induction, including sarcopenia, cataracts, and loss of adipose tissue (Baker et al., *Nat. Cell Biol.*, 10:825-836 (2008)). Treated mice of both BubR1$^{H/H}$:INK-ATTAC lines exhibited substantially delayed onset of lordokyphosis (a measure of sarcopenia in this model) and cataracts compared to untreated mice, which developed these phenotypes at a rate similar to BubR1$^{H/H}$ mice lacking the INK-ATTAC transgene (FIGS. 5B and 5C). Consistent with decreased lordokyphosis, muscle fiber diameters of AP20187-treated BubR1$^{H/H}$:INK-ATTAC animals were larger than those of untreated counterparts (FIG. 5D). In addition to muscle retention, treadmill exercise tests revealed that duration of exercise (FIG. 5E), distance traveled (FIG. 5F), and overall amount of work performed (FIG. 5G) were all significantly increased in the animals treated with AP20187, indicating preservation of muscle function. Dual-energy x-ray absorptiometry (DEXA) scans of BubR1$^{H/H}$:INK-ATTAC mice confirmed that AP20187 treatment prevented loss of adipose tissue (FIG. 5H). All major fat deposits were larger in AP20187-treated BubR1$^{H/H}$:INK-ATTAC animals (FIG. 5H), and individual adipocytes were markedly increased in size (Figure SI). Consistent with this generally increased adiposity, dorsal skin contained significantly more adipose tissue (FIG. 5J).

Age-related phenotypes of BubR1$^{H/H}$ mice that arise in a p16$^{Ink4a}$-independent fashion, such as cardiac arrhythmias and arterial wall stiffening (Matsumoto et al., *Stroke*, 38:1050-1056 (2007)), were not attenuated in AP20187-treated BubR1$^{H/H}$:INK-ATTAC-3 and BubR1$^{H/H}$:INK-ATTAC-5 mice (FIGS. 6A and 6B). This correlated with lack of INK-ATTAC induction in heart and aorta (FIGS. 1C and 6B). Cardiac failure is presumably the main cause of death in BubR1$^{H/H}$ mice, which could explain why the overall survival of AP20187-treated BubR1$^{H/H}$:INK-ATTAC mice was not substantially extended (FIG. 6C). To examine whether clearance of p16$^{Ink4a}$-positive cells might have any overtly negative side effects, WT:INK-ATTAC mice were continuously treated with AP20187 until eight months of age. No such overtly negative side effects were observed. Taken together, these results indicated that continuous removal of p16$^{Ink4a}$-expressing cells from BubR1$^{H/H}$:INK-ATTAC mice selectively delays age-related phenotypes that depend on p16$^{Ink4a}$ induction.

The following was performed to determine whether the delayed onset of age-related pathologies coincided with a reduction in the number of senescent cells in these tissues. TAT of AP20187-treated BubR1$^{H/H}$:INK-ATTAC mice exhibited a dramatic decrease in SA-β-Gal staining compared with TAT of untreated counterparts (FIG. 7A). Corresponding decreases of other senescence-associated markers were also observed, as well as expected reductions in INK-ATTAC and GFP (FIGS. 7B and 8A). Skeletal muscle (FIGS. 7C and 8B) and eye (FIGS. 7D and 8C) exhibited a similar reduction in senescence indicators. BrdU incorporation was lower in TAT and muscle tissue of untreated than in treated animals (FIG. 7E), further supporting the contention that senescence-associated replicative arrest is decreased upon administration of AP20187 in BubR1$^{H/H}$:

INK-ATTAC transgenic animals. Together, these results indicated that senescent cells were cleared from tissues and that this delays acquisition of age-related dysfunction in BubR1 hypomorphic mice.

The results provided herein demonstrate the generation of a transgenic mouse model that allows for the inducible removal of p16$^{Ink4a}$-positive senescent cells. By breeding this model into a progeroid mouse genetic background, the clearance of p16$^{Ink4a}$-expressing senescent cells selectively was shown to delay onset of age-related pathologies in tissues that accumulate these cells, demonstrating that development of age-related pathologies and cellular senescence are clearly linked in this model. These results also demonstrate that therapeutic interventions to clear senescent cells or block their effects represent an avenue for treating or delaying age-related diseases and improving healthy human lifespan.

Methods and Materials

The INK-ATTAC transgenic construct was made as follows. The FKBP-Casp8 fragment was subcloned from the aP2-ATTAC transgenic construct (Pajvani et al., Nat. Med., 11:797-803 (2005)), and inserted into pBlueScriptII (Stratagene). A 2617-bp segment of the murine p16$^{Ink4a}$ promoter was PCR amplified from BAC DNA to replace the aP2 promoter. An IRES-EGFP fragment was inserted 3' of the ATTAC. Nine transgenic founder lines of mice were obtained by injection of this construct into FVB oocytes using standard methods. A PCR-based method was used for INK-ATTAC transgene identification. BubR1$^{H/H}$ mice were generated as described elsewhere (Baker et al., Nat. Genet., 36:744-749 (2004)). For AP20187 (ARIAD Pharmaceuticals, Inc.; Cambridge, Mass.) treatments, animals were injected intraperitoneally (i.p.) every three days with 0.2 µg/g body weight of the dimer-inducing drug (Pajvani et al., Nat. Med., 11:797-803 (2005)). All mice were on a mixed 129×C57BL6×FVB genetic background. Animals were housed in a pathogen-free barrier environment throughout the study. Experimental procedures involving the use of laboratory mice were reviewed and approved by the appropriate committee. GraphPad Prism software was used for generating survival curves and for statistical analyses.

Cell Culture

Bone marrow cells were obtained by flushing of tibia and femur bones of 2-month-old WT:INK-ATTAC transgenic mouse lines and cultured as described elsewhere (Soleimani and Nadri, Nat. Protoc., 4:102-106 (2009)). In brief, after washing by centrifugation at 400×g for 10 minutes and counting of viable cells with trypan blue, cells were resuspended in DMEM containing 15% FBS to a final concentration of 5×10$^6$ viable cells per mL. Initially, cells were plated in 6-well tissue culture dishes at 3.5 mL/well (1.9× 10$^6$ cells/cm$^2$). Cultures were kept in a humidified 5% CO$_2$ incubator at 37° C. for 72 hours, when non-adherent cells were removed by changing the medium. Assays were performed on cells that had been trypsinized and seeded to confluency in 24-well plates. To induce senescence and evaluate expression of the INK-ATTAC transgene, cells were treated with 1 µM rosiglitazone (Cayman Chemical Company, Ann Arbor, Mich.) or with vehicle. The accumulation of GFP-positive cells was observed by fluorescence microscopy. After 5 days of rosiglitazone treatment, cells were then washed with PBS and treated with vehicle, 1 µM rosiglitazone, 10 nM AP20187, or both. After 48 hours, cultures were fixed and stained for SA-β-Gal activity as described elsewhere (Dimri et al., Proc. Natl. Acad. Sci. USA, 92:9363-9367 (1995)).

qRT-PCR and Flow Cytometry

RNA extraction, cDNA synthesis, and qRT-PCR from whole-mouse tissue were performed as described elsewhere (Baker et al., Nat. Cell Biol., 10:825-836 (2008)). To perform qRT-PCR on GFP$^+$ and GFP$^-$ cell populations of IAT, single-cell suspensions of stromal vascular fraction were prepared from about 50 mg IAT as described elsewhere (Kirkland et al., Int. J. Obes. Relat. Metab. Disord., 20(Suppl 3):5102-107 (1996)). GFP$^+$ and GFP$^-$ cells were then separated and collected using a FACS Aria Cell Sorter running FACSDiva software (BD Biosciences). RNA was extracted from these cells using an RNeasy Micro Kit (Qiagen), and cDNA synthesized using a WT-Ovation RNA Amplification kit (NuGEN Technologies, Inc.) according to the manufacturers' protocols.

qRT-PCR primers were as follows: FKBP-Casp8 forward, GAATCACAGACT-TTGGACAAAGTT (SEQ ID NO:25); FKBPCasp8 reverse, GGTCAAAGCCCCT-GCATCCAAG (SEQ ID NO:26); EGFP forward, CAAACTACAACAGC-CACAACG (SEQ ID NO:27); and EGFP reverse, GGT-CACGAACTCCAGCAG (SEQ ID NO:28). Sequences of other primers used were as described elsewhere (Baker et al., Nat. Cell Biol., 10:825-836 (2008)). Statistical differences were determined using two-tailed unpaired t tests.

Analysis of Progeroid Phenotypes

Bi-weekly checks for lordokyphosis and cataracts were performed as described elsewhere (Baker et al., Nat. Cell Biol., 10:825-836 (2008)). Skeletal muscle fiber diameter measurements were performed on cross sections of gastrocnemius and abdominal muscles of female mice (n=6 mice per genotype). Fifty total fibers per sample were measured using a calibrated computer program (Olympus MicroSuite Five). Fat cell diameter measurements were performed on IAT according to the same method. Dissection, histology, and measurements of dermal and adipose layers of dorsal skin were performed as described elsewhere (Baker et al., Nat. Genet., 36:744-749 (2004)). Measurements of body weight, length, gastrocnemius muscle, and assorted adipose deposits were performed on 8-10-month-old females (n=6 per genotype). Bone mineral content, bone mineral density, and total body adipose tissue were analyzed by DEXA scanning as described elsewhere (Krishnamurthy et al., J. Clin. Invest., 114:1299-1307 (2004)) (n=6 per genotype). Exercise measurements were performed on 8-10-month-old mice as described elsewhere (Handschin et al., J. Biol. Chem., 282:30014-30021 (2007); and LeBrasseur et al., J. Gerontol. A. Biol. Sci. Med. Sci., 64:940-948 (2009)). Animals were acclimated for three days for 5 minutes at a speed of 5 m/minute prior to experimentation. For the experiment, the speed of the treadmill began at 5 m/minute and was increased to 8 m/minute after 2 minutes. Thereafter, the speed was increased at a rate of 2 m/minute every 2 minutes, and the time (in seconds) and distance (in meters) to exhaustion, as defined by an inability to move along the treadmill with stimulation, were determined. The formula to determine the amount of work (J) performed was: mass (kg)*g (9.8 m/s$^2$)*distance (m)*sin(θ) (with an incline of θ=5°).

In Vivo BrdU Incorporation and SA-β-Gal Staining

Analyses for in vivo BrdU incorporation were performed in 8-10-month-old female mice (n=6 per genotype) as described 13. Adipose tissue depots were stained for SA-β-Gal activity as described elsewhere (Baker et al., Nat. Cell Biol., 10:825-836 (2008)).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A transgenic mouse for studying the role of senescent cells in an age-related phenotype, the genome of which contains a transgene, said transgene containing a p16$^{INK4a}$ promoter sequence operably linked to a nucleic acid sequence encoding a polypeptide so as to cause said polypeptide to be expressed in senescent cells in said mouse, wherein said polypeptide directly induces cell death in cells in which said polypeptide is expressed when activated by a compound, and wherein administration of said compound to said mouse activates said polypeptide, thereby directly inducing cell death in senescent cells and inducing cell death in less than 10% of non-senescent cells, whereby progression of said age-related phenotype is delayed in said mouse relative to another such transgenic mouse that is not administered said compound.

2. The transgenic mouse of claim 1, wherein said polypeptide comprises a caspase 8 polypeptide sequence.

3. The transgenic mouse of claim 1, wherein said polypeptide comprises an FKBP polypeptide sequence.

4. The transgenic mouse of claim 1, wherein said polypeptide is an FKBP-caspase 8 fusion polypeptide.

5. The transgenic mouse of claim 1, wherein said compound is AP20187.

6. The transgenic mouse of claim 1, wherein the genetic background of said transgenic mouse is a BubR1$^{H/H}$ genetic background.

7. The transgenic mouse of claim 1, wherein said transgene comprises nucleic acid encoding a marker polypeptide.

8. The transgenic mouse of claim 7, wherein said marker polypeptide is a GFP polypeptide.

9. A transgenic mouse, the genome of which contains a transgene, that comprises:
(a) a p16INK4a promoter sequence operably linked to a nucleic acid sequence encoding a polypeptide that directly induces cell death in cells in which said polypeptide is expressed when activated by a compound; and (b) an internal ribosome entry site (IRES) sequence followed by a nucleic acid sequence encoding a marker polypeptide;

wherein senescent cells in said mouse express both said polypeptide and said marker polypeptide, and wherein administration of said compound to said transgenic mouse activates said polypeptide, thereby directly inducing cell death in senescent cells and inducing cell death in less than 10% of non-senescent cells; whereby progression of an age-related phenotype is delayed in said mouse relative to another such transgenic mouse that is not administered said compound.

10. The transgenic mouse of claim 9, wherein the polypeptide comprises a caspase 8 polypeptide sequence.

11. The transgenic mouse of claim 9, wherein the polypeptide comprises an FKBP polypeptide sequence.

12. The transgenic mouse of claim 9, wherein the polypeptide is an FKBP-caspase 8 fusion polypeptide.

13. The transgenic mouse of claim 9, wherein the compound is AP20817.

14. The transgenic mouse of claim 9, wherein the genetic background of the transgenic mouse is a BubR1$^{H/H}$ genetic background.

15. The transgenic mouse of claim 9, wherein the marker polypeptide is a GFP polypeptide.

16. The transgenic mouse of claim 1, wherein the age-related phenotype is sarcopenia.

17. The transgenic mouse of claim 1, wherein the age-related phenotype is a cataract.

18. The transgenic mouse of claim 1, wherein the age-related phenotype is loss of adipose tissue.

19. The transgenic mouse of claim 9, wherein the age-related phenotype is sarcopenia.

20. The transgenic mouse of claim 9, wherein the age-related phenotype is a cataract.

21. The transgenic mouse of claim 9, wherein the age-related phenotype is loss of adipose tissue.

22. A method for removing senescent cells from a tissue, comprising contacting said tissue with a compound, wherein the genome of cells in said tissue contains a recombinant nucleic acid in which a p16INK4a promoter sequence controls expression of a polypeptide so as to cause said polypeptide to be expressed in senescent cells, wherein said polypeptide directly induces cell death in cells in which said polypeptide is expressed when activated by said compound, and wherein contacting said tissue with said compound directly induces cell death in senescent cells and induces cell death in less than 10% of non-senescent cells, whereby progression of an age-related phenotype is delayed in said tissue as a result of contacting said tissue with said compound.

23. The method of claim 22, wherein said promoter in said recombinant nucleic acid controls expression of a marker polypeptide.

24. The method of claim 23, wherein said marker polypeptide is a GFP polypeptide.

25. A method of determining whether delayed onset of an age-related phenotype coincides with a reduction in the number of senescent cells in a tissue, said method comprising:
(a) obtaining a plurality of mice according to claim 1;
(b) treating a proportion of the mice in said plurality with said compound, thereby directly inducing cell death in senescent cells in the treated mice; and
(c) imaging or measuring a sign of the age-related phenotype in the treated mice or in the mice that were untreated.

26. The method of claim 25, wherein said compound is AP20187.

27. The method of claim 25, wherein said age-related phenotype is expression of senescence-related markers in inguinal adipose tissue (IAT).

28. The method of claim 27, wherein said sign is staining for senescence-associated beta-galactosidase (SA β Gal).

29. The method of claim 25, wherein said age-related phenotype is replicative arrest.

30. The method of claim 29, wherein said sign is lower incorporation of BrdU.

31. A method of determining whether delayed onset of an age-related phenotype coincides with a reduction in the number of senescent cells in a tissue, said method comprising:
(a) obtaining a plurality of mice according to claim 9;
(b) treating a proportion of the mice in said plurality with said compound, thereby directly inducing cell death in senescent cells in the treated mice; and
(c) imaging or measuring a sign of the age-related phenotype in the treated mice or in the mice that were untreated.

* * * * *

UNITED STATES PATENT AND TRADEMARK OFFICE
CERTIFICATE OF CORRECTION

PATENT NO. : 9,968,076 B2  
APPLICATION NO. : 14/792208  
DATED : May 15, 2018  
INVENTOR(S) : James L. Kirkland et al.

Page 1 of 1

It is certified that error appears in the above-identified patent and that said Letters Patent is hereby corrected as shown below:

In the Claims

Column 39, Line 20, please delete "AP20817" and replace it with -- AP20187 --

Signed and Sealed this
Twelfth Day of February, 2019

Andrei Iancu
*Director of the United States Patent and Trademark Office*